US008609600B2

(12) United States Patent
Warr et al.

(10) Patent No.: US 8,609,600 B2
(45) Date of Patent: Dec. 17, 2013

(54) ENCAPSULATION OF BULKY FRAGRANCE MOLECULES

(75) Inventors: Jonathan Warr, Paris (FR); Emmanuel Aussant, Paris (FR); Stuart Fraser, Cheshire (GB)

(73) Assignee: Takasago International Corporation, Tokyo (JP)

( * ) Notice: Subject to any disclaimer, the term of this patent is extended or adjusted under 35 U.S.C. 154(b) by 770 days.

(21) Appl. No.: 11/849,696

(22) Filed: Sep. 4, 2007

(65) Prior Publication Data

US 2008/0176780 A1  Jul. 24, 2008

(30) Foreign Application Priority Data

Sep. 4, 2006  (EP) .................................... 06300921

(51) Int. Cl.
*C11D 9/44* (2006.01)
*C11D 3/50* (2006.01)
*C11D 3/00* (2006.01)

(52) U.S. Cl.
USPC ........... 510/103; 510/101; 510/100; 510/505; 510/102; 512/4; 424/401

(58) Field of Classification Search
USPC ........ 512/4, 1, 8–20; 510/221, 100–106, 438, 510/505, 513, 515, 520; 424/401, 76.6, 424/76.1, 76.4, 45; 426/89, 92, 94, 96
See application file for complete search history.

(56) References Cited

U.S. PATENT DOCUMENTS

| 2,800,457 | A | 7/1957 | Green et al. |
|---|---|---|---|
| 3,415,758 | A | 12/1968 | Powell et al. |
| 4,234,627 | A | 11/1980 | Schilling |
| 6,261,483 | B1 | 7/2001 | Frank et al. |
| 2003/0036489 | A1* | 2/2003 | Liu et al. ........................ 510/100 |
| 2003/0055143 | A1* | 3/2003 | Mori et al. ..................... 524/381 |
| 2004/0072719 | A1 | 4/2004 | Bennett et al. |
| 2005/0153135 | A1 | 7/2005 | Popplewell et al. |
| 2005/0226900 | A1* | 10/2005 | Winton Brooks et al. .... 424/401 |
| 2005/0227907 | A1* | 10/2005 | Lee et al. ........................... 512/4 |
| 2006/0039934 | A1 | 2/2006 | Ness et al. |
| 2006/0154378 | A1 | 7/2006 | Lei et al. |
| 2007/0149423 | A1 | 6/2007 | Warr et al. |
| 2007/0149424 | A1 | 6/2007 | Warr et al. |

FOREIGN PATENT DOCUMENTS

| EP | 0385535 | A1 | 9/1990 |
|---|---|---|---|
| EP | 1407754 | A1 | 4/2004 |
| EP | 1533415 | A1 | 5/2005 |
| EP | 1589092 | A1 | 10/2005 |
| EP | 1661978 | A1 | 5/2006 |
| WO | 9734987 | A1 | 9/1997 |
| WO | 02085420 | A1 | 10/2002 |
| WO | 2004016234 | A1 | 2/2004 |

OTHER PUBLICATIONS

European Search Report dated Sep. 30, 2008.

\* cited by examiner

*Primary Examiner* — James J Seidleck
*Assistant Examiner* — S. Camilla Pourbohloul
(74) *Attorney, Agent, or Firm* — Sughrue Mion, PLLC

(57) ABSTRACT

A fragrance composition to be incorporated into the core of a core shell capsule, including:

I) 60-100% by weight of at least 5 different fragrance compounds, each of the at least 5 different fragrance compounds possessing any of the structural features a) to g) defined in the specification, and II) 0-40% by weight of other benefit agents which possess any of the structural features a) to g), pro-fragrances, and solvents.

23 Claims, No Drawings

ENCAPSULATION OF BULKY FRAGRANCE MOLECULES

FIELD OF THE INVENTION

The invention relates to compositions to be incorporated into the core of core shell type capsules to control the delivery and release of fragrance and optionally other benefit agents, when used as components within household, personal care and cosmetic products. Chiefly, the invention relates to core shell capsules made by the condensation of formaldehyde with melamine and/or urea as the major monomers around an emulsion of the core materials, however this is not intended to exclude capsules made by other processes such as coacervation, or precipitation or to limit the monomers used to synthesize the capsule wall to amines and aldehydes.

The invention further relates to the use of these capsules in household cleaners, laundry products, personal care and cosmetic products in the form of liquids, gels, creams, powders or soft solids; in which the delivery and release of the fragrance and optionally other benefit agents is controlled.

BACKGROUND OF THE INVENTION

Is it known to encapsulate water insoluble perfumes or other materials, in small capsules often termed microcapsules, typically having a diameter less than 1000 micrometers (microns), for a variety of reasons relating to the protection, delivery and release of the perfume or other material. The preparation of microcapsules is described in Kirt Othmer's Encyclopaedia of Chemical Technology 5$^{th}$ edition and also in the following U.S. Pat. No. 2,800,457 and U.S. Pat. No. 3,415,758 and citations thereof and U.S. Pat. No. 6,261,483 and references therein. One type of capsule, referred to as a wall or shell or core shell capsule, comprises a generally spherical shell of water and oil insoluble material, typically a network polymer material, within which perfume or other material is contained.

If such capsules are incorporated in consumer products containing certain solvents and/or emulsifiers or surfactants, e.g. personal care products such as deodorants, hair sprays or shampoos, laundry products such as fabric conditioners or liquid laundry detergents and household cleaners such as kitchen surface cleaners, problems can arise with the encapsulated material tending to leach out of the capsules and be solubilised in the product over time diminishing the capsules delivery of their core materials.

U.S. Pat. No. 4,234,627 teaches the incorporation of hydrophobic non polymeric materials with the fragrance to control perfume release. However this involves a dilution of the fragrance or benefit agent.

US patent application 20060154378 relates to a method for measuring the leaching of encapsulated material in an application medium using a dialysis or filtration to separate the active ingredient molecules from the capsules.

US patent application 20050153135 teaches a variety of methods to reduce perfume leaching by formulating the fragrance from materials which are substantially water insoluble, by adding an oil or polymer to the fragrance to reduce the partitioning. While such measures reduce the rate of escape they do not prevent it and they may have other undesirable consequences such as reducing the impact of the fragrance.

US patent application 20060039934 teaches that adding polymers, either to the core contents prior to encapsulation, or the exterior of the capsules can reduce leakage. Again this adds to the cost and processing complexity involved in manufacturing capsules.

Notwithstanding these teaching terse is still a need for ways to minimize the loss of fragrance during storage and the present invention aims to address such stability problems.

SUMMARY OF THE INVENTION

It is an object of the present invention to provide a fragrance composition that can be incorporated into a core shell capsule so that on storage in household cleaners, laundry products, personal core and cosmetic products, in the form of liquids, gels, creams or soft solids, little of the fragrance escapes into the product on storage, but which does not affect the performance of the capsule in use.

Surprisingly this can be achieved by formulating fragrances with a high proportion of bulky molecules, i.e. a mixture of molecules which by virtue of the arrangement of atoms within the molecules are too bulky or inflexible to pass readily through the capsule walls. To be effective a significant proportion of the fragrance must be composed of bulky molecules of the invention.

DETAILED DESCRIPTION OF THE INVENTION

Namely, the present invention relates to the following items 1 to 22.

1. A fragrance composition to be incorporated into the core of a core shell capsule comprising:

I) 60-100% by weight of at least 5 fragrance compounds, 20-100% by weight of said fragrance compounds comprising at least 3 bulky molecules having a molecular weight of less than 325 atomic mass units, conforming to the following structures:

a) molecules containing more than one ring, each ring having between 3 and 8 atoms of any of carbon, oxygen, nitrogen or sulfur in any ring and atoms being shared by any of the rings;

b) molecules having at least two rings, each ring having between 3 and 8 atoms of any of carbon, oxygen, nitrogen or sulfur in which any rings share a common atom;

c) molecules having at least two rings, each ring having between 3 and 8 atoms of any carbon, oxygen, nitrogen or sulfur in which any two rings share at least two adjacent common atoms;

d) molecules containing a single alicyclic ring which contains at least 5 atoms, but no more than 8 atoms, of any of carbon, oxygen, nitrogen and sulfur in which at least one of the carbon atoms of the ring has two substituents, or a carbon atom alpha to the ring is tertiary carbon atom, or the ring has substituents on at least three of the atoms which make up the ring;

e) molecules containing at least one macrocyclic ring, which is a ring having more greater than eight atoms of any of carbon, nitrogen oxygen or sulfur in the ring;

f) molecules containing at least one substituted aromatic ring containing at least 5 atoms of any of carbon, oxygen, nitrogen or sulfur, but in which at least one substituents has a tertiary carbon in a position alpha or beta to the ring;

g) molecules containing a substituted aromatic ring comprising at least 5 atoms with at least 3 substituents groups on the ring all of which must contain at least 2 atoms from among carbon, oxygen, nitrogen or sulfur; and II) 0-40% by weight of pro-fragrances, solvents, and other benefit agents which possess any of the structural features a) to g) but are not constrained by the molecular weight restrictions.

2. The fragrance composition according to item 1, wherein the molecular weights of the individual fragrance ingredients lie within the range 100 to 300 atomic mass units and 80% to 100% by weight of bulky molecules have C log P values greater than 1.0.

3. The fragrance composition according to item 1, wherein the molecular weights of the individual fragrance ingredients lie within the range 100 to 275 atomic mass units and 80% to 100% by weight of bulky molecules have C log P values greater than 1.0.

4. A fragrance composition to be incorporated into the core of a core shell capsule comprising 60-100% by weight of bulky molecules according to item 1.

5. A fragrance composition to be incorporated into the core of a core shell capsule comprising 80-100% by weight of bulky molecules according to item 1.

6. A fragrance composition to be incorporated into the core of a core shell capsule comprising:
I) 60-100% by weight of at least 5 fragrance compounds, 20-100% by weight of said fragrance compounds comprised of at least 3 bulky molecules having a molecular weight of less than 275 atomic mass units, processing any of the following structural features:
  a) molecules containing more than one ring, each containing 5 or 6 carbon atoms, no atoms being shared by any of the rings;
  b) molecules having at least two rings, each having between 3 and 6 atoms in which any rings share a common atom;
  c) molecules having at least two rings, each ring containing 5 or 6 carbon atoms in which two rings share at least two adjacent common atoms;
  d) molecules containing a single alicyclic ring which contains at least 5 atoms, but no more than 8 atoms, of any of carbon, oxygen, nitrogen and sulfur in which at least one of the carbon atoms of the ring has two substituents, or a carbon atom alpha to the ring is tertiary carbon atom, or the ring has substituents on at least three of the atoms which make up the ring;
  e) molecules containing at least one macrocyclic ring, which is a ring having more greater than eight atoms in the ring;
  f) molecules containing at least one substituted benzene ring but in which at least one substituents group processes a tertiary carbon in a position alpha or beta to the ring; and
II) 0-40% by weight of pro-fragrances, solvents, and other benefit agents which possess any of the structures a) to f) but are not constrained by the molecular weight restrictions.

7. The fragrance composition according to item 1 or 6, wherein 40-100% by weight of the fragrance ingredients have C log P values between C log P 1.00 and C log P 4.00.

8. The fragrance composition according to item 1 or 6, wherein 60-100% by weight of the fragrance ingredients have C log P values between C log P 1.00 and C log P 4.00.

9. The fragrance composition according to item 1 or 6, wherein 80-100% by weight of the fragrance ingredients have C log P values between C log P 1.00 and C log P 4.00.

10. The fragrance composition according to item 1 or 6, wherein more than 25% of the originally encapsulated amount by weight of the individual fragrance components survive storage for 4 weeks at 40° C., when dosed at 0.5% of encapsulated fragrance oil when dispersed in a 10% (wt/wt) aqueous solution of sodium dodecyl sulfate buffered at pH of 8.5.

11. The fragrance composition according to item 1 or 6, wherein more than 50% of the originally encapsulated amount by weight of the individual fragrance components survive storage for 4 weeks at 40° C., when dosed at 0.5% of encapsulated fragrance oil when dispersed in a 10% (wt/wt) aqueous solution of sodium dodecyl sulfate buffered at pH of 8.5.

12. The fragrance composition according to item 1 or 6, containing 0-40% weight of one or more benefit agents in which the benefit agents are selected among the group consisting of molodor counteracting agents, essential oils, aromatherapeutic materials, chemoesthetic agents, vitamins, insect repellents, pro-fragrances, UV absorbers, antioxidants and agents to improve the capsule properties such as:
  a) by stabilizing the emulsion during capsule manufacture,
  b) by reducing leakage from the capsule,
  c) by improving capsule hardness.

13. The fragrance composition according to item 1 or 6, wherein the fragrance contains less than 20% by weight of aldehydes.

14. The fragrance composition according to item 1 or 6, wherein the fragrance contains less than 10% by weight of amines.

15. An encapsulated fragrance comprising a core shell having a thickness of 0.025-1.0 μm and a fragrance composition according to item 1 or 6.

16. The encapsulated fragrance according to item 15, wherein the capsule shell is an aminoplast capsule constituted of 50-100% by weight of formaldehyde-melamine or formaldehyde-melamine-urea or formaldehyde-urea condensation polymer.

17. The encapsulated fragrance according to item 15, wherein the average size of the capsule is between 1-1000 micrometers.

18. A household, laundry or personal care composition which is in the form of a liquid, gel, paste, soft solid, or liquid applied to a fibrous substrate such as a wipe, containing one or more of surfactants and/or solvents containing the core shell capsule according to any one of items 1 to 17.

19. The household, laundry or personal care composition according to item 18, which is in the form of a liquid having a viscosity greater than 100 mPa·s at 5 s$^{-1}$.

20. The household, laundry or personal care composition according to item 18, which is in the form of a liquid having a viscosity greater than 1000 mPa·s at 5 s$^{-1}$.

21. The household, laundry or personal care composition according to item 18, wherein the composition is a liquid laundry detergent, a liquid fabric softener, a hair shampoo, a hair conditioner, a liquid soap, a shower gel, or a liquid impregnated on household or personal care wipes.

22. A method for delivering perfume to surfaces, which comprises contacting the surface with the composition according to any one of items 18 to 20 with the capsule containing composition according to any one of items 1 to 17, optionally diluted with water, or delivered from a suitable washing appliance in such a way that the capsules release their contents either directly on application or subsequently.

The followings explains the present invention in detail.

Perfume Composition

In the context of this specification a "perfume composition", which is also named "fragrance composition", is an essential part of the invention. The term "perfume composition" means any mixture, i.e. more than one chemical species, including materials which act as malodor counteractants. A wide variety of odiferous materials are known for perfumery use, including materials such as alkenes, alcohols, aldehydes, ketones, esters, ethers, nitrites, amines, oximes, acetals, ketals, thiols, thioketones, imines, etc. Without wishing to be limited, the ingredients of the perfume composition will have molecular weights of than 325 atomic mass units, preferably less than 300 atomic mass units and more preferably less than 275 atomic mass units to ensure sufficient volatility to be noticeable when the capsules release. Furthermore the perfume compounds will have molecular weights greater than 100 atomic mass units, preferably greater than 120 atomic mass units as lower masses may be too volatile or too water soluble. Ingredients of the fragrance compositions will not contain strongly ionizing functional groups such as sulfonates, sulfates, or quaternary ammonium ions.

Naturally occurring plant and animal oils and exudates comprising complex mixtures of various chemical components are also know for use as perfumes, and such materials can be used herein. The principal chemical components of most naturals are know within ranges), and thus for the most part they can be assessed in the same way as synthetic aroma chemicals. Perfume compositions of the present invention can be relatively simple in their composition with a minimum of two perfume or fragrance ingredients or can comprise highly complex mixtures of natural and synthetic chemical components, chosen to provide any desired odor. It is preferred if the perfume composition contains more than 5 components, more preferable that they contain more than 8 components. Perfume ingredients are described more fully in S. Arctander, Perfume Flavors and Chemicals. Vols. I and II, Montclair, N.J., and the Merck Index, $8^{th}$ Edition, Merck & Co., Inc. Rahway, N.J., both are incorporated herein by reference.

Bulky Fragrance Molecules

Bulky molecules of invention are defined as molecules suitable for use in perfumery having molecular arrangements of atoms which either by arrangement of atoms or conformational rigidity render them incapable, or only capable of passing very slowly, through the capsule shell. Considering a molecule's possible conformations in 3 dimensions, the ration of length to width and depth must be such that irrespective of the orientation of the molecule it will not pass through the capsule shell. Many molecules can adopt orientations which will allow them to pass through small gaps, For example a molecule such as n-hexanol can adopt various conformations because al of the methylene fragments are relatively such as cyclohexanol the methylene units are constrained to be less flexible.

An isomer of n-hexanol, 2,2-dimethybutanol is also more bulky than hexanol because of the substitution pattern within the molecule. These aspects of stereochemistry are well known to those skilled in the art and are taught in many standard textbooks such as "Organic Chemistry" by Clayden, Greeves, Warren and Wothers Oxford University Press 2001. The compounds of the invention seemingly by virtue of the arrangement of atoms either by having branching side chains or possessing ring structures within the molecules have been found to escape to more limited degree through the walls of care shell capsules when stored in liquid products containing surfactants and/or solvents than other perfumery molecules not possessing these features. Compounds of the invention exhibit any of the following molecular structural features a) to g) and can be defined as follows:

a) Molecules Containing More than One Ring, Each Ring Having Between 3 and 8 Atoms of any Carbon, Oxygen, Nitrogen or Sulfur in any Ring.

Molecules must contain more than one cyclic structure or ring. Rings must have between 3 and 8 atoms which may include atoms other than carbon, so called heterocyclic rings which might include oxygen, nitrogen or sulfur atoms. The rings may be aromatic i.e. derived from benzene or naphthalene, heteroaromatic e.g. pyridine, pyrazine, furan, thiophen, thiazoles, ozazoles etc., alicyclic, optionally including unsaturation within any of the rings, so cycloalkanes or cycloalkenes e.g. cyclopentanes, cyclopentenes, cyclohexanes or cyclohezenes, tetrahydrofurans, morpholines, dioxins, piperidines, pyrans etc. or any mixture of the above. Hydrogen atoms on any of the rings may be substituted by carbon, oxygen, nitrogen or sulfur atoms in the usual range of organic functional groups, ethers, alcohols, esters, aldehydes, ketones, acetals, ketals, oximes, amines, amides, nitriles, thiols and thioethers.

For the purposes of this patent the following terms are defined as follows:

Alkyl is the univalent group left when a hydrogen atom is removed from an aliphatic hydrocarbon such and menthyl, $CH_3$— from, ethane and $C_2H_5$— from ethane. They have the general formula $C_nH_{2n+1}$.

Alkyldiyl is the divalent group formed by removing two hydrogen atoms either from two different carbon atoms or from a single carbon atom in an aliphatic hydrocarbon such as methylene, —$CH_2$— from methane and ethyldiyl —$C_2H_4$— from ethane. They have the general form $C_nH_{2n}$.

Alkenyl is the univalent group left when a hydrogen atom is removed from an aliphatic alkene such as propenyl, $CH_2$=$CH$—$CH_2$— from propane. Unless specified substituents may have either cis or trans stereochemistry or may be a mixture of the stereoisomers.

Alkenyldiyl is the divalent group formed by removing two hydrogen atoms either from two different carbon atoms or from a single carbon atom in an aliphatic alkene such as propenylene $CH_2$=$CH$—$CH$= or propendiyl as for example —$CH$=$C$=$CH$— from propene. Unless specified substituents may have either cis or trans stereochemistry or may be a mixture of the stereoisomers.

Heterocyclic group is the univalent group formed by removing a hydrogen atom from any ring atom of an heterocyclic compound (compounds having as ring members atoms of at least two different elements).

Aryl is the monovalent group derived from an arene (a monocyclic or polycyclic aromatic hydrocarbon) by removal of a hydrogen from a ring carbon atom.

Heteroaryl is the group left when a hydrogen atom is removed from an heteroarene (Heteroarenes are aromatic heterocyclic compounds formally derived from arenas by replacement of one or more methane (—C=) and/or vinylene (—CH=CH—) groups by trivalent or divalent hetero atoms respectively in such a way as to maintain the continuous π electron system characteristic of aromatic systems.

Cyclic or ring systems are a series of atoms which form a closed ring e.g. cyclohexane rather than the open chain aliphatic compound. Aromatic rings are those capable of undergoing electrophilic substitution reactions rather than the addition reactions which occur with non-aromatic unsaturated compounds. They can also be defined as planar rings having (4n+2)π electrons according to Huckels rule and include arenas and heteroarenes.

The term substituted which is used throughout this specification means a substituents unit which has replaced hydrogen and for the purposes of the present invention substituents are defined as chemical moieties which can replace a hydrogen atom on an aliphatic hydrocarbon chain, an alicyclic ring, an aryl ring, an heteroaryl ring, an heterocyclic ring and the like, or replacement of hydrogen atom, two hydrogen atoms or three hydrogen atoms from a carbon atom to form a moiety or the replacement of hydrogen atoms from adjacent carbon atoms to form a moiety. For example a substituents that replaces a single hydrogen atom includes halogen, hydroxyl, and the like. A two hydrogen atom replacement on a single carbon atom includes carbonyl or imine and the like, while an example of a substituents that replaces a hydrogen on each of two adjacent carbons in an epoxide. It is quite likely that substituents replace hydrogens on atoms which may themselves be part of a substituents on another unit. For example in 2-phenylethanol the hydroxyl unit is a substituents on an alkyl chain which is itself substituent on a benzene ring.

The following are non limiting example of substituents:
—OH; —OR'; —CN; =O; —SR'; =S; =NOH;

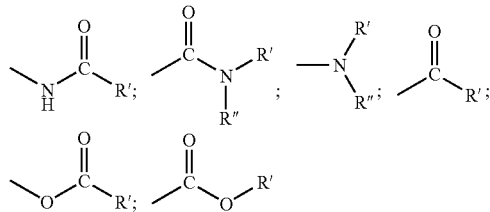

wherein R' and R" can be independently hydrogen or $C_1$-$C_6$ linear or branched alkyl or $C_2$-$C_6$ linear or branched alkenyl, or $C_5$-$C_{10}$ carbocyclic, heterocyclic, aryl, or heteroaryl moieties.

Further definitions of chemical nomenclature can be found in "G. P. Moss, P. A. S. Smith and D. Tavernier, Pure and Applied Chemistry, Vol. 67 pp 1307-1375 1995."

Examples of Bulky Molecules as Defined in Item a) are Perfume Compounds Having Molecular Formulae of Structure 1:

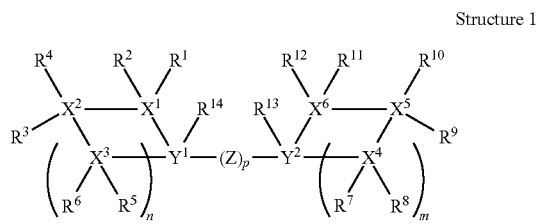

Structure 1

Wherein:
$Y^1$ or $Y^2$ can be independently carbon or nitrogen atoms and
$X^1$ to $X^6$ can be independently carbon, nitrogen, oxygen or sulfur atoms;
Z can be any of:
 $C_1$-$C_6$ substituted or unsubstituted linear alkyldiyl;
 $C_2$-$C_6$ substituted or unsubstituted linear alkenyldiyl;
 $C_2$-$C_6$ substituted or unsubstituted branched alkyldiyl;
 $C_2$-$C_6$ substituted or unsubstituted branched alkenyldiyl;
an ether comprising unit having the following formulas:

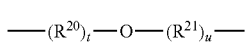  (1)

an ester comprising unit having either of the following formula:

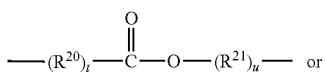  (2)
or

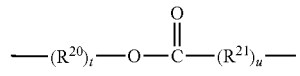  (3)

a carbonyl comprising unit having the following formula:

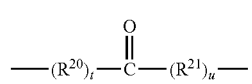  (4)

an imine comprising unit having the following formula:

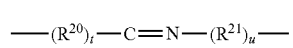  (5)

wherein in formulas (1) to (5), $R_{20}$ and $R_{21}$ can independently represent:
 $C_1$-$C_6$ substituted or unsubstituted linear alkyldiyl;
 $C_2$-$C_6$ substituted or unsubstituted linear alkenyldiyl;
 $C_2$-$C_6$ substituted or unsubstituted branched alkyldiyl;
 $C_2$-$C_6$ substituted or unsubstituted branched alkenyldiyl;
while t and u can be independently 0 or 1;
 p may equal 0 or 1; when p equals 0 there is a direct link between atoms in the two rings which may be a single or double bond; (If it is a double bond then $Y^1$ and $Y^2$ must be carbon and $R^{13}$ and $R^{14}$ are absent);
 m and n are independently integers between 0 to 5;
 $R^1$ to $R^{14}$ may be present depending upon the valency requirements of the atoms represented by X and Y and any unsaturation or aromaticity within any of the rings;
where present $R^1$ to $R^{14}$ may be independently:
 hydrogen, methyl or substituted methyl
 $C_2$-$C_8$ substituted or unsubstituted linear alky;
 $C_2$-$C_8$ substituted or unsubstituted linear alkenyl;
 $C_3$-$C_8$ substituted or unsubstituted branched alkyl;
 $C_3$-$C_8$ substituted or unsubstituted branched alkenyl;
 $C_4$-$C_8$ substituted or unsubstituted cycloalkyl;
 $C_4$-$C_8$ substituted or unsubstituted cycloalkenyl;
 $C_5$-$C_8$ substituted or unsubstituted aryl;
 $C_6$-$C_8$ substituted or unsubstituted alkaryl;
 $C_6$-$C_8$ substituted or unsubstituted heterocycloalkyl;
 hydroxy;
an ether comprising a unit having the following formula:

an ester comprising unit having either of the following formulas:

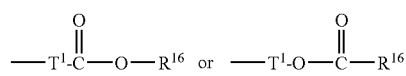

a carbonyl comprising unit having the following formula:

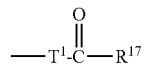

a ketal comprising unit substituted directly onto a ring having the following formula:

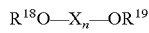

in which case $X_n$ is a carbon atom, n being 1, 2, 3, 4, 5, or 6;
an acetal or ketal comprising unit having the following formula:

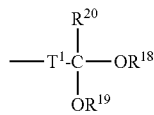

a nitrile comprising unit having the following formula:

wherein:
$T^1$ is direct bond, a $C_1$-$C_6$ linear or branched alkyldiyl group or a $C_2$-$C_6$ alkenyldiyl group;
$R^{15}$, $R^{16}$, $R^{18}$ and $R^{19}$ can be:
Methyl or substituted methyl,
$C_2$-$C_8$ substituted or unsubstituted linear alky;
$C_2$-$C_8$ substituted or unsubstituted linear alkenyl;
$C_3$-$C_8$ substituted or unsubstituted branched alkyl;
$C_3$-$C_8$ substituted or unsubstituted branched alkenyl;
$C_4$-$C_8$ substituted or unsubstituted cycloalkyl;
$C_4$-$C_8$ substituted or unsubstituted cycloalkenyl;
$C_5$-$C_8$ substituted or unsubstituted aryl;
$C_6$-$C_8$ substituted or unsubstituted alkaryl;
$C_6$-$C_8$ substituted or unsubstituted heterocycloalkyl;
$R^{17}$ and $R^{20}$ can be hydrogen or $R^{15}$;
$R^{18}$ and $R^{19}$ can also be taken together to form a $C_3$ to $C_6$ spiroannulated ring.

In addition, any of $R^1$ to $R^{14}$ may be combined with any other R either on the same or a different carbon atom (X) to form further rings. Thus molecules of this aspect of the invention are not limited to two rings. Moreover the radicals $R^1$ and $R^2$; $R^3$ and $R^4$; $R^5$ and $R^6$; $R^7$ and $R^8$; $R^9$ and $R^{10}$; $R^{11}$ and $R^{12}$ together with the atom X to which they are linked can form a carbonyl group.

Thus molecules of this aspect of the invention have more than one ring which may be joined by a bond between any two atoms of either ring, i.e. p equals zero as in Acetoketal (Takasago; 2,5,5-Trimethyl-2-phenyl1,3-dioxane), or they may be linked by groups such as ethers as in diphenyl oxide, esters as in benzyl benzoate and α,β-unsaturated esters as in cinnamyl cinnamate, or imines as in Lyrome (IFF; Methyl n-{4-(4-hydroxy-4-methylpentyl)-3-cyclohexen-1-methylene}-anthranilate).

In the compounds having structure 1, it is preferred if the majority of X atoms are carbon and at least one of m or n equals 3, more preferably both m and n equal 3, wherein at least one or preferably both rings contains 6 atoms. It is especially preferred if the rings are cyclohexyl or benzene rings or a mixture of the two either of which may contain substituent groups. It is also preferred in structure 1 if Z is an alkyl ester as in benzyl salicylate or phenylethyl phenylacetate or cinnamyl cinnamate.

Without wishing to be restricted in any way this group may be exemplified by Diphenyl oxide (101-84-8), Benzyl salicylate (118-58-1), Cyclohexyl salicylate (25485-88-5), Phenyl ethyl phenylacetate (102-20-5), Methyl n-{4-(4-hydroxy-4-methylpentyl)-3-cyclohexen-1-methylene}-anthranilate (Lyrame; IFF) (67634-12-2), Endo 4-(5-Methyl1-5-Norbornen-2-yl)-pyridine (Orriniff; IFF) (125352-06-9), 2,5,5-Trimethyl-2-phenyl1,3-dioxane (Acetoketal; Takasago) (5406-58-6), Isocamphyl cyclohexanol (Santalex T; Takasago) (68877-29-2), 2-(2,4-Dimethyl-3-cyclohexyl)-5-methyl-5-(1-methylpropyl)-1,3-dioxane (Karanal; Quest) (117933-89-8), Vanillin propylene glycol acetal (68527-74-2), Indol-Hydroxycitronellal Schiff's base (Indolene50; IFF) (68908-82-7), Dimethyl-2-(5',5',8',8'-tetramethyl-5',6',7',8'-tetrahydro-naphthalen-2'-yl) 1,3-dioxolane (Okoumal; Givaudan) (131812-67-4), Cyclohexyl anthranilate (7779-16-0), 2-Cyclohexylidene-2-phenylacetonitrile (10461-98-0), Cyclohexyl cinnamate (7791-17-1), Benzyl cinnamate (103-41-3), Benzyl eugenol (120-11-6), Cinnamyl anthranilate (87-29-6), Cinnamyl cinnamate (122-69-0), Cinnamyl phenyl acetate (7492-65-1), 4-Methyl-2-phenyltetrahydro-2H-pyran (Doremox; Firmenich) (24720-09-0), Dibenzyl ketone (102-04-5), and Benzophenone (119-61-9).

b) Molecules Having at Least Two Rings, Each Ring Having Between 3 and 8 Atoms of any of Carbon, Oxygen, Nitrogen or Sulfur in which any Two Rings Share a Common Atom.

Molecules having this structural feature are termed spiroannulated rings and the shared carbon atom C is termed a spiro atom. For the invention spiroannulated rings must contain between 3 and 8 atoms which may include atoms other than carbon, so called heterocyclic rings, these might include one or more atoms from oxygen, nitrogen or sulfur in ether ring. The spiroannulated rings are alicyclic but may optionally including unsaturation within either or both rings as exemplified by cycloalkanes, cycloalkenes, dihydrofurans or tetrahydrofurans, morpholines, dioxins, piperidines, oxazolidines or quinolines. Hydrogen atoms on any of the rings may be substituted by carbon, nitrogen, oxygen, or sulfur atoms in the usual range of organic functionalities: alkane, alkene, and alikene groups, ethers, alcohols, esters, aldehydes, ketones, acetals, ketals, oximes, amines, amides, nitriles, yhiols and thioethers.

Example of the Bulky Molecules as Defined in Item b) are Perfume Compound Having Molecular Formulas as in Structure 2.

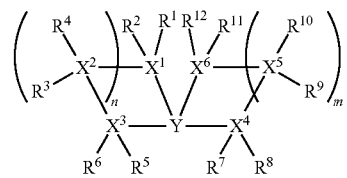

Structure 2

Wherein,
Y is carbon;
$X^1$ to $X^6$ can be independently carbon, nitrogen, oxygen or sulfur atoms;
any of $R^1$ to $R^{12}$ may not be present depending upon the valency requirements of the atoms represented by X and unsaturation or aromaticity within either of the rings;
where present $R^1$ to $R^{12}$ may be independently:
hydrogen, methyl or substituted methyl
$C_2$-$C_8$ substituted or unsubstituted linear alky;
$C_2$-$C_8$ substituted or unsubstituted linear alkenyl;
$C_3$-$C_8$ substituted or unsubstituted branched alkyl;
$C_3$-$C_8$ substituted or unsubstituted branched alkenyl;
$C_4$-$C_8$ substituted or unsubstituted cycloalkyl;
$C_5$-$C_8$ substituted or unsubstituted cycloalkenyl;
$C_6$-$C_8$ substituted or unsubstituted aryl;
$C_6$-$C_8$ substituted or unsubstituted alkaryl;
$C_6$-$C_8$ substituted or unsubstituted heterocycloalkyl;
hydroxy;

an ether comprising a unit having the following formula:

in which the $T^1$ and $R^{15}$ are as defined hereinabove for Structure 1;

an ester comprising unit having either of the following formulas:

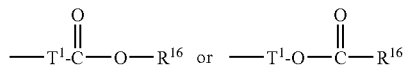

in which the $T^1$ and $R^{16}$ are as defined hereinabove for Structure 1;

a carbonyl comprising unit having the following formula:

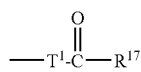

in which the $T^1$ and $R^{17}$ are as defined hereinabove for Structure 1;

a ketal comprising unit substituted directly onto a ring having the following formula:

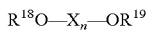

in which case $X_n$ is a carbon atom, n being 1, 2, 3, 4, 5, or 6;

an acetal or ketal comprising unit having the following formula:

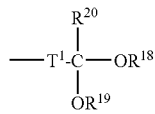

in which the $T^1$, $R^{18}$, $R^{19}$ and $R^{20}$ are as defined hereinabove for Structure 1;

a nitrile comprising unit having the following formula:

in which the $T^1$ is as defined hereinabove for Structure 1;

In addition, any of $R^1$ to $R^{12}$ may be combined with any other R either on the same or a different carbon atom (X) to form further rings. Thus molecules of this aspect of the invention are not limited to two rings. Moreover the radicals $R^1$ and $R^2$; $R^3$ and $R^4$; $R^5$ and $R^6$; $R^7$ and $R^8$; $R^9$ and $R^{10}$; $R^{11}$ and $R^{12}$ together with the atom X to which they are linked can form a carbonyl group.

Thus molecules of this aspect of the invention are defined by sharing a common carbon atom as in spirodecane. In the compounds having structure 2, it is preferred if the majority of X atoms are carbon and at least one of m or n equals 2 or 3. It is also preferred if $X^4$ and $X^6$ are independently oxygen or nitrogen atoms as in 1,3-dioxans or 1,3-oxazolines.

Without wishing to be restricted in any way this group may be exemplified by 2-Methyl-1,5-dioxaspiro[5.5]undecane (Spirodecane; IFF) (6413-26-9), 2,2,3',7',7'-Pentamethyl-spiro(1,3-dioxan-5,2'-norcarane) (Spirambrene; Givaudan) (12151-67-0 or 12151-68-1), Decahydro-spiro[furan-2(3H), 5-(4,7-methano-5H-indene)] (Vigoflor; IFF) (68480-11-5), 3,3-Dimethyl-1,5-Dioxaspiro[5.5]undecane (707-29-9), 4-Methyl-1-oxaspiro[5.5]undecene (Oxaspirane; IFF) (68228-06-8), 8-Methyl-1-Oxaspiro[4.5]decan-2-one (94201-19-1)

c) Molecules Having at Least Two Rings, Each Ring Having Between 3 and 8 Atoms of any of Carbon, Oxygen, Nitrogen or Sulfur in which any Two Rings Share at Least Two Adjacent Common Atoms.

Rings must have between 3 and 8 atoms which may include atoms other than carbon; so called hetrocyclic rings, these might include one or more atoms of oxygen, nitrogen or sulfur in any ring. The rings may be aromatic i.e. derived from, naphthalene, indole, pyridine, pyrazine furan, thiophen, thiazoles, ozazoles or alicyclic optionally including unsaturation within either or both rings exemplified by cycloalkanes and cycloalkenes, tetrohydrofurans, morpholines, dioxanes, piperidines, quinolines, pyrans etc. or a mixture of aromatic and alicyclic rings as exemplified by indans and dihydrocoumarins which may also optionally include unsaturation within the rings. Hydrogen atoms on any of the rings may be substituted by carbon, nitrogen, oxygen or sulfur aroma in the usual range of organic functionalities: alkane, alkene, and alkyne groups, ethers, alcohols, esters, aldehydes, ketones, acetals, ketals, oximes, amines, amides, nitriles, thiols and thioethers. Bridged molecules having structures exemplified by [2,2,1]bicycloheptane and [3,2,1]bycyclooctane are also within this aspect of the invention as they share more than one common atom between the rings. Examples of the Bulky Molecules as Defined in Item c) are the Perfume Compounds Having Molecular Formulas as in Structure 3.

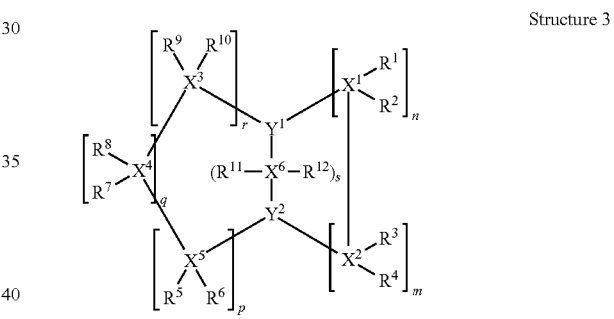

Structure 3 wherein:
$Y^1$ and $Y^2$ can be independently carbon or nitrogen atoms;
$X^1$ to $X^6$ can be independently carbon, nitrogen, oxygen or sulfur atoms;
s equals 0 to 3; when s equals 0 there is one bond or two atoms (Y—Y) shared between two rings which may be a single or double bond or part of an aromatic bond as in naphthalenic molecules;
m, n, p, q and r are independently integers between 0 to 2;
$R^1$ to $R^{12}$ may or may not be present depending upon the valency requirements of the atoms represented by X and Y, and any unsaturation or aromaticity within any of the rings;
where present $R^1$ to $R^{12}$ may be independently:
hydrogen, methyl or substituted methyl
$C_2$-$C_8$ substituted or unsubstituted linear alky;
$C_2$-$C_8$ substituted or unsubstituted linear alkenyl;
$C_3$-$C_8$ substituted or unsubstituted branched alkyl;
$C_3$-$C_8$ substituted or unsubstituted branched alkenyl;
$C_4$-$C_8$ substituted or unsubstituted cycloalkyl;
$C_5$-$C_8$ substituted or unsubstituted cycloalkenyl;
$C_6$-$C_8$ substituted or unsubstituted aryl;
$C_6$-$C_8$ substituted or unsubstituted alkaryl;
$C_6$-$C_8$ substituted or unsubstituted heterocycloalkyl;
hydroxy;

an ether comprising a unit having the following formula:

in which the $T^1$ and $R^{15}$ are as defined hereinabove for Structure 1;

an ester comprising unit having either of the following formulas:

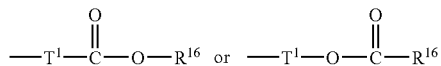

in which the $T^1$ and $R^{16}$ are as defined hereinabove for Structure 1;

a carbonyl comprising unit having the following formula:

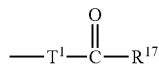

in which the $T^1$ and $R^{17}$ are as defined hereinabove for Structure 1;

a ketal comprising unit substituted directly onto a ring having the following formula:

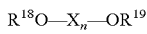

in which case $X_n$ is a carbon atom, n being 1, 2, 3, 4, 5, or 6;

an acetal or ketal comprising unit having the following formula:

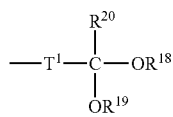

in which the $T^1$, $R^{18}$, $R^{19}$ and $R^{20}$ are as defined hereinabove for Structure 1;

a nitrile comprising unit having the following formula:

in which the $T^1$ is as defined hereinabove for Structure 1;

In addition, any of $R^1$ to $R^{12}$ may be combined with any other R either on the same or a different carbon atom (X) to form further rings. Thus molecules of this aspect of the invention are not limited to two rings. Moreover the radicals $R^1$ and $R^2$; $R^3$ and $R^4$; $R^5$ and $R^6$; $R^7$ and $R^8$; $R^9$ and $R^{10}$; $R^{11}$ and $R^{12}$ together with the atom X to which they are linked can form a carbonyl group.

Examples of fragrance ingredients of this category are 2-Naphthyl methyl ether (yara yara) (93-04-9), Coumarin (91-64-5), Methyl naphthyl ketone (941-98-0), Isobutylquinoline (65442-31-1), 1,3,4,6,7,8-Hexahydro-4,6,6,7,8,8-hexamethyl-cyclopenta-γ-2-benzopyran (Galaxolide; IFF) (01222-05-5), 6-Acetyl-1,1,2,4,4,6-hexamethyl tetrahydronaphthalene (Tonalide; PFW) (021145-77-7), 6,7-Dihydro-1,1,2,3,3-pentamethyl-4(5H)-indanone (Cashmeran; IFF) (033704-61-9), Tricyclo decenyl acetate (Cyclacet; IFF) (5413-60-5) and its homologues Tricyclo decenyl propionate (Cyclaprop; IFF) (17511-60-3) and Tricyclo decenyl isobutyrate (Cyclabute; IFF) (067634-20-2), Cedryl methyl ether (Cedramber; IFF) (019870-74-7), 4-(1,3-Benzodioxol-5-yl) butan-2-one (Dulcinyl; IFF) (55418-52-5) 3a-Ethyl dodecahydro-6,6,9a-trimethyl naphtho[2,1-b]-furan (Grisalva; IFF) (68611-23-4), 2,5,5-Trimethyl-octahydronaphthalen-2-ol (Ambrinol 20-T; Takasago) (41199-19-3), β-Caryophyllene (13877-93-5), Caryophyllene (87-44-5), Caryophyllene acetate (57082-24-3), α-Cedrene (469-61-4), 8-Cedren-13-ol (28231-03-0), Cedrol (77-53-2), Cedryl acetate (77-54-3), Cedrenyl acetate (1405-92-1), Cedryl formate (39900-38-4), Cedryl methyl ether (67874-81-1), α-Methyl-3,4-methylenedioxy hydrocinnamic aldehyde, (Heliobouquet; Takasago) (1205-17-0), Ethyl tricyclo[5,2,1,0]decan-2-carboxylate (Frutate; Kao) (080657-64-3), 1,4-Cineole (470-67-7), 1,8-Cineole (470-82-6), Borneol (464-45-9), Bornyl acetate (76-49-3), Isoborneol (124-76-5), Isobornyl acetate (125-12-2), Isobornyl formate (1200-67-5), Isobornyl methyl ether (5331-32-8), Isobornyl propionate (2756-56-1), 2-Ethyl-5(or 6)-methoxy bicyclo[2.2.1]heptane and 1-Ethyl-3-methoxy tricyclo[2.2.1.0$^{2,6}$]heptane (Neoproxen; IFF) (122795-41-9), 2-Ethylidene-6-isopropoxy bicyclo[2.2.1]heptane (Isoproxen; IFF) (90530-04-4), 5' (or 6')-(Methylnorborn-5'-en-2'-yl)-2-menthyl-1-en-3-ol (Florosantal; Takasago) (67739-11-1 and 85232-76-4), 2-[(1,7,7-Trimethybicyclo[2,2,1]hept-2-yl)oxy]-ethanol (Cedanol; Takasago) (7070-15-7), Fenchyl alcohol (1632-73-1), Decahydro-3a,6,6,9a-tetramethyl naphtho[2,1-b]furan (Ambrox; Firmenich) (6790-58-5), 7-Acetyl-1,2,3,4,5,6,7,8-octahydro-1,1,6,7-tetramethyl-naphthalene (Iso E Super; IFF) (54464-57-2), Patchouli alcohol (5986-55-0), Norpathoulenol (41429-52-1), Isobornyl cyclohexanol (Santalex T; Takasago) (68877-29-2), 2,2,7,7-Tetramethyltricyclo[6.2.1.0$^{1,6}$]undecane-5-one (Isolongifolanone; Quest) (23787-90-8), Octahydro-7,7,8,8-tetramethyl-2,3b-methano-3bH-cyclopenta(1,3)cyclopropa(1,2)benzene-4-methyl acetate (Amboryl acetate) (59056-62-1), Nootkatone (Givaudan) (4674-50-4), 9-Ethylidene-3-oxatricyclo[6.2.1.0$^{2,7}$]undecane-4-one (Florex; Firmenich) (69486-14-2), Cedryl methyl ether (19870-74-7 and 67874-81-1), α-Pinene (80-56-8), β-Pinene (127-91-3), 5,6,7,7a-Tetrahydro-4,4,7a-trimethyl-2(4H)-benzofuranone (Dihydroactinidolide) (15356-74-8), 1,3-Dimethyl-8-(-methylethyl)-tricyclo[4.4.0.0.0$^{2,7}$]dec-3-ene (α-Copaene) (3856-25-5), Camphene (79-92-5), Camphor (464-49-3), 5-Acetyl-1,1,2,3,3,6-hyxamehyl indan (Phantolide; PFW) (15323-35-0), 4-Acetyl-6-tertiary-butyl-1,1-dimethyl indane (Celestolide; IFF) (13171-00-1), 5-Acetyl-1,1,2,6-tetramethyl-3-isopropyl-dihydroinden (Traseolide; Quest) (68140-48-7), 6-Acetyl-1,1,2,4,4,6-hexamethyl tetrahydronaphthalene (Tonalide; PFW) (21145-77-7), β-Nephthyl isobutyl ether (2173-57-1), Decahydro-β-naphthyl acetate (10519-11-6), 6-Methoxydicyclopentadiene carboxaldehyde (Scentenal; Firmenich) (86803-90-9), 4-Methyl tricyclo[6.2.1.0]undecan-5-one (Plicatone; Firmenich) (41724-19-0), 3,4,4a,5,8,8a-Hexahydro-3',7'-dimethyl spiro(1,4-methanonaphthalene-2(1H),2'-oxirane) (Rhubofix; Firmenich) (41815-03-9), Dodecahydro-3a,6,6,9a-Tetramethyl-Naphto[2,1-b]Furan (Cetalox; Firmenich) (3738-00-9), 6-Ethylidene octahydro-5,8-methano-2H-1-benzopyran-2-one (Florex; Firmenich) (69486-14-2).

d) Molecules Containing a Single Alicyclic Ring which Contains at Least 5 Atoms, but No More than 8 Atoms, of any of Carbon, Nitrogen, Oxygen and Sulfur in which at Least One of the Carbon Atoms of the Ring has Two Substituents i.e. it is a Tertiary Carbon Atoms, or a Carbon Atom Alpha to the Ring is a Tertiary Carbon Atoms, or the Ring has Substituents on at Least Three of the Atoms which Make Up the Ring.

The ring may optionally contain more than 3 substituents. The ring may contain heterocyclic atoms and optionally unsaturated bonds and the substituents may be alkyl or alkenyl or aryl groups, or functional groups such as hydroxyl, ether, aldehyde, ketone, acetal, amine, amide, nitrile, oxime, thio, or thioether.

Examples of Bulky Molecules as Defined in Item d) are Perfume Compounds Having Molecular Formulas as in Structures 4 or 5.

Structure 4

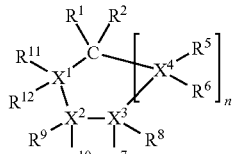

Structure 5

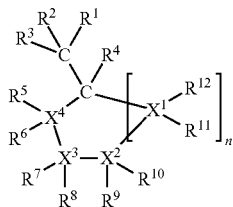

wherein:
any of $X^1$ to $X^4$ independently represents carbon, nitrogen, oxygen or sulfur atoms;
C represents a carbon atoms;
n equals 1 to 4 but is preferably 2 or 3;
$R^1$, $R^2$ and $R^3$ can be any of the following:
hydrogen, methyl or substituted methyl
$C_2$-$C_8$ substituted or unsubstituted linear alky;
$C_2$-$C_8$ substituted or unsubstituted linear alkenyl;
$C_3$-$C_8$ substituted or unsubstituted branched alkyl;
$C_3$-$C_8$ substituted or unsubstituted branched alkenyl;
$C_4$-$C_8$ substituted or unsubstituted cycloalkyl;
$C_5$-$C_8$ substituted or unsubstituted cycloalkenyl;
$C_6$-$C_8$ substituted or unsubstituted aryl;
$C_6$-$C_8$ substituted or unsubstituted alkaryl;
$C_6$-$C_8$ substituted or unsubstituted heterocycloalkyl;
hydroxy;
an ether comprising a unit having the following formula:

in which the $T^1$ and $R^{15}$ are as defined hereinabove for Structure 1;
an ester comprising unit having either of the following formulas:

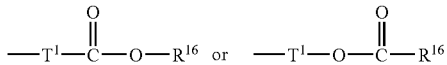

in which the $T^1$ and $R^{16}$ are as defined hereinabove for Structure 1;
a carbonyl comprising unit having the following formula:

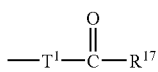

in which the $T^1$ and $R^{17}$ are as defined hereinabove for Structure 1;

a ketal comprising unit substituted directly onto a ring having the following formula:

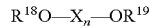

in which case $X_n$ is a carbon atom, n being 1, 2, 3 or 4;
an acetal or ketal comprising unit having the following formula:

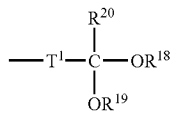

in which the $T^1$, $R^{18}$, $R^{19}$ and $R^{20}$ are as defined hereinabove for Structure 1;
a nitrile comprising unit having the following formula:

in which the $T^1$ is as defined hereinabove for Structure 1;
$R^4$ to $R^{12}$ can be hydrogen or $R^1$.
The radicals $R^1$ and $R^2$; $R^3$ and $R^4$; $R^5$ and $R^6$; $R^7$ and $R^8$; $R^9$ and $R^{10}$; $R^{11}$ and $R^{12}$ together with the atom X to which they are linked can form a carbonyl group.

In the compounds having structure 4 or 5, it is preferred if the majority of X atoms are carbon and n equals 1 or 2.

Examples of fragrance molecules which meet this definition are: Para-tertiary-butyl-cyclohexanol (98-52-2), Para-tertiary-butyl-cyclohexyl acetate (32210-23-4), Ortho-tertiary-butyl-cyclohexanol (13491-79-7), Ortho-tertiary-butyl-cyclohexyl acetate (88-41-5), Para-tertiary-butyl-cyclohexanone (98-53-3), Methyl dihydrojasmonate (Hedione; Firmenich) (24851-98-7), α-Ionone (127-41-3), β-Ionone (14901-07-6) and γ-Ionone (79-76-5), α-Damascone (24720-09-0), β-Damascone (23726-92-3), δ-Damascone (57378-68-4), γ-Damascone (35087-49-1), β-Damascenone (23696-85-7), 2-Ethyl-4-(2,2,3-trimethyl-3-cyclopenten-1-yl)-2-buten-1-ol (Bacdanol; IFF) (28219-61-6), 4-Acetoxy-4-methyl-2-propyl-tetrahydro-2H-pyran (Clarycet; IFF) (131766-73-9), Ortho tertiary amyl cyclohexanyl acetate (Coniferan; IFF) (67874-72-0), 2,4-dimethylcyclohexanemethanol (Dihydrofloralol) (68480-15-9), 3-Methyl-5-(2,2,3-trimethyl-3-cyclopenten-1-yl)-4-penten-2-ol (Ebanol; Givaudan) (67801-20-1), Ethyl acetoacetate propylene glycol acetal (Fraistone; IFF) (6290-17-1), Isocyclogeraniol (IFF) (68527-77-5), 5-Methyl-3-butyltetrahydro-pyran-4-yl acetate (Jasmelia; IFF) (58285-49-3), Fenchol (22627-95-8), Fenchyl acetate (13851-11-1), (–)-2-Ethyl-4-(2,2,3-trimethyl-3-cyclopenten-1-yl)-2-buten-1-ol (Levosandol; Takasago) (28219-61-6), Ethylacetoacetate ethyleneglycol ketal (6413-10-1), Nopol (128-50-7), Nopyl acetate (35836-72-7), 2,6,6-Trimethyl-1-cyclohexen-1-acetoaldehyde (472-66-2), 2,4,6-Trimethyl-3-cyclohexene-1-carboxaldehyde (1335-66-6), 2,4,6-Trimethyl-3-cyclohexene-1-methanol (68527-77-5), 3-Methyl-5-propyl-2-cyclohexen-1-one (3720-16-9), Dynascone (Firmenich) (56973-85-4), α-Iso-methyl-ionone (1335-46-9), 3,3-Dimethyl-5-(2',2',3'-trimethyl-3'-cyclopenten-1'-yl)-4-penten-2-ol (Polysantol; Firmenich) (107898-54-4), 2,2-dimethyl-6-methylene cyclohexane carboxylic acid methyl ester (Romascone; Firmenich) (81752-87-6), 5-Pentyl-2,2,5-trimethylcyclopentanone (65443-14-3), 2,2,6-Trimethyl-α-propyl-cyclohexanepropanol (Timberol; Symrise) (70788-30-6), 2-tert-Butyl cyclohexyl oxy-2-butanol (Amber Core; Kao) (139504-68-0), Myrac aldehyde (Precyclimone B; IFF) (52474-60-9), 2-Methyl-4-(2,6,6-trimethyl-1-cyclohexen-1- yl)-2-Butenal (Boronal; Symrise) (3155-71-3), 2,2,5-Trimethyl-5-pentylcyclopentanone (65443-14-3), β-2,2,3-Tetramethyl-3-Cyclopentene-1-butanol (Brahmanol; Symrise) (72089-08-8), 2-Methyl-4-(2,2,3-trimethyl-3-cyclopenten-1-yl)-2-buten-1-ol (Sandalmysore core; Kao) (28219-60-5), 3-Methyl-5-(2,2,3-trimethyl cyclopent-3-en-1-yl-pentan-2-ol (Sandolare; Givaudan) (65113-99-7), 4-tert-Pentylcyclohexanone (16587-71-6), 4-(1-ethoxyvinyl)-3,3,5,5-tetramethyl cyclohexanone (Kaphalis; Givaudan) (36306-87-3), Ethyl 2-tert-butyl cyclohexyl carbonate (Floramat; Cognis) (67801-64-3), Methyl 2-hexyl-3-oxocyclopentanecarboxylate (Jasmapol; PFW) (37172-53-5), 3-Oxo-2-(2-cis-pentenyl)cyclopentane acetic acid methyl ester (1211-29-6), 2-Pentyl-3-methyl-2-cyclopenten-1-one (1128-08-1).

e) Molecules Containing at Least One Macrocyclic Ring; i.e. a Ring with More Greater than 8 Atoms of Any of Carbon, Nitrogen, Oxygen and Sulfur in the Ring.

The ring may contain carbon, nitrogen, oxygen or sulfur atoms and include functional groups such as unsaturation, lactones, ethers, amides, The macrocyclic ring may also contain substituents based on carbon, nitrogen, oxygen and sulfur groups such as alkyl and alkenyl groups, alcohols, esters, ethers, aldehydes, ketones, acetals, amides, amides, nitriles, aximes, thiols and thioether.

Example of Bulky Molecules as Defined in Item e) are Perfume Compounds Having Molecular Formulas as in Structure 6:

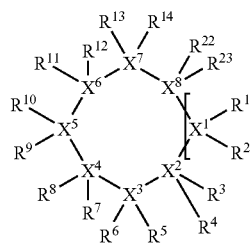

Structure 6 wherein:
  $X^1$ represents a carbon atoms;
  any of $X^1$ to $X^8$ independently represents carbon, nitrogen, oxygen or sulfur atoms;
  n is an integer between 1 to 8;
  $R^1$ to R14, R22 and R23 can be independently any of the following, or they may not be present depending upon the valency requirements of the atoms represented by the corresponding X and any unsaturation within the ring:
    hydrogen, methyl or substituted methyl
    $C_2$-$C_8$ substituted or unsubstituted linear alky;
    $C_2$-$C_8$ substituted or unsubstituted linear alkenyl;
    $C_3$-$C_8$ substituted or unsubstituted branched alkyl;
    $C_3$-$C_8$ substituted or unsubstituted branched alkenyl;
    $C_4$-$C_8$ substituted or unsubstituted cycloalkyl;
    $C_5$-$C_8$ substituted or unsubstituted cycloalkenyl;
    $C_6$-$C_8$ substituted or unsubstituted aryl;
    $C_6$-$C_8$ substituted or unsubstituted alkaryl;
    $C_6$-$C_8$ substituted or unsubstituted heterocycloalkyl;
    hydroxy;
    an ether comprising a unit having the following formula:

-$T^1$-$OR^{15}$ in which the $T^1$ and $R^{15}$ are as defined hereinabove for Structure 1;
    an ester comprising a unit having either of the following formulas:

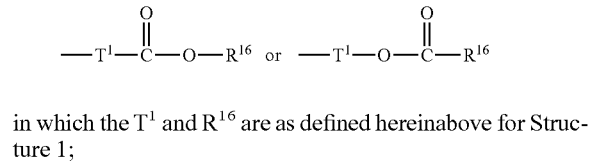

in which the $T^1$ and $R^{16}$ are as defined hereinabove for Structure 1;
    a carbonyl comprising unit having the following formula:

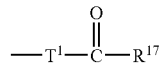

in which the $T^1$ and $R^{17}$ are as defined hereinabove for Structure 1;
    a nitrile comprising unit having the following formula:

-$T^1$-C≡N in which the $T^1$ is as defined hereinabove for Structure 1;
  or the radicals $R^1$ and $R^2$; $R^3$ and $R^4$; $R^5$ and $R^6$; $R^7$ and $R^8$; $R^9$ and $R^{10}$; $R^{11}$ and $R^{12}$; $R^{13}$ and $R^{14}$; $R^{22}$ and $R^{23}$ together with the atom X to which they are linked can form a carbonyl group.

Examples of such molecules include Ethylene Brassylate (Musk T; Takasago) (105-95-3), 3-Methylcyclopentadecanone (Muscone) (541-91-3), 3-Methylcyclopentadecenone (Muscenone) (82356-51-2), 3-Methylcyclopentadecanol (Muscol) (4727-17-7), Cyclopentadecanolide (Exaltolide; Firmenich) (106-02-5), Cyclopentadecanone (Exaltone; Firmenich) (502-72-7), (Z)-4-Cyclopentadecen-1-one (Exaltenone; Firmenich) (14595-54-1), Trimethyl-oxabicyclotridecadiene (Cedroxyde; Firmenich) (71735-79-0), 15-Pentadecenolide (34902-57-3), (Z)-9-Cycloheptadecen-1-one (542-46-1), 12-Methyl-14-tetradec-9-enolide, Oxacycloheptadec-7(or 10)-en-2-one (Ambrettolide; IFF) (28645-51-4), 5-Cyclohexadecen-1-one (Ambretone; Takasago) (37609-25-9), [3(or 4)-Cycloocten-1-yl]methyl carbonate (Violiff; IFF) (87731-18-8), Methyl 2,6,10-trimethylcyclododeca-2,5,9-trien-1-yl ketone (Trimofix O; IFF) (28371-99-5), Cyclodecyl methyl ether (2986-54-1), Ethoxymethoxycyclidodecane (5867-11-6).

f) Molecules Containing at Least One Substituted Aromatic Ring Containing at Least 5 Atoms of any of Carbon, Nitrogen, Oxygen or Sulfur, but in which at Least One Substituent has a Tertiary Carbon in a Position Alpha or Bate to the Ring.

Examples of Bulky Molecules as Defined in Item f) are Perfume Compounds Having Molecular Formulas as in Structure 7:

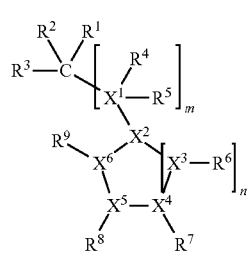

Structure 7 wherein:
  any of $X^1$ to $X^6$ independently represents carbon, nitrogen, oxygen or sulfur atoms;
  n equals an integer between 1 and 3;
  m equals an integer between 0 and 1;

R4 to R9 need not be present depending upon the valency requirements of the atoms represented by X;

R¹, R² and R³ may be:
hydrogen, methyl or substituted methyl
$C_2$-$C_8$ substituted or unsubstituted linear alky;
$C_2$-$C_8$ substituted or unsubstituted linear alkenyl;
$C_3$-$C_8$ substituted or unsubstituted branched alkyl;
$C_3$-$C_8$ substituted or unsubstituted branched alkenyl;
$C_4$-$C_8$ substituted or unsubstituted cycloalkyl;
$C_5$-$C_8$ substituted or unsubstituted cycloalkenyl;
$C_6$-$C_8$ substituted or unsubstituted aryl;
$C_6$-$C_8$ substituted or unsubstituted alkaryl;
$C_6$-$C_8$ substituted or unsubstituted heterocycloalkyl;
hydroxy;
an ether comprising a unit having the following formula:

-T¹-OR¹⁵ in which the T¹ and R¹⁵ are as defined hereinabove for Structure 1;

an ester comprising unit having either of the following formulas:

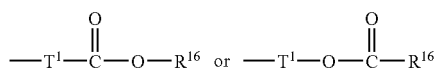

in which the T¹ and R¹⁶ are as defined hereinabove for Structure 1;

a carbonyl comprising unit having the following formula:

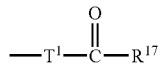

in which the T¹ and R¹⁷ are as defined hereinabove for Structure 1;

a nitrile comprising unit having the following formula:

-T¹-C≡N in which the T¹ is as defined hereinabove for Structure 1;

R⁴ to R⁹ can be independently hydrogen or R¹.

Examples of such molecules are: 2-Methyl-3-(4-tert-butylphenyl)propanal (Lilial; Givaudan) (80-54-6), 2,5,5-Trimethyl-2-phenyl1,3-dioxane (Acetoketal; Takasago) (5406-58-6), 4-tert-Butylbenzennpropionaldehyde (18127-01-0), Dimethybenzylcarbinyl acetate (151-05-3), 5-Phenyl-5-methyl-3-hexanone (Damascol 4; IFF) (4927-36-0).

g) Molecules Containing a Substituted Ring Comprising at Least 5 Atoms with at Least 3 Substituted Groups on the Ring all of which Must Contain at Least 2 Atoms from Among Carbon, Nitrogen, Oxygen or Sulfur.

Examples of Bulky Molecules as Defined in Item g) are Perfume Compounds Having Molecular Formulas as in Structure 8:

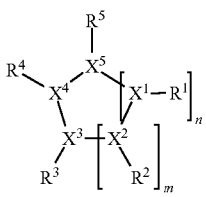

Structure 8 wherein:
any of X¹ to X⁵ independently represents carbon, nitrogen, oxygen or sulfur atoms;
n is an integer between 1 and 3; and
m is an integer between 1 and 2.
R¹ to R⁵ need not be present depending upon the valency requirements of the atoms represented by the relevant X, when present; at least three of R¹ to R⁵ must be independently:
hydrogen, methyl or substituted methyl
$C_2$-$C_8$ substituted or unsubstituted linear alky;
$C_2$-$C_8$ substituted or unsubstituted linear alkenyl;
$C_3$-$C_8$ substituted or unsubstituted branched alkyl;
$C_3$-$C_8$ substituted or unsubstituted branched alkenyl;
$C_4$-$C_8$ substituted or unsubstituted cycloalkyl;
$C_5$-$C_8$ substituted or unsubstituted cycloalkenyl;
$C_6$-$C_8$ substituted or unsubstituted aryl;
$C_6$-$C_8$ substituted or unsubstituted alkaryl;
$C_6$-$C_8$ substituted or unsubstituted heterocycloalkyl;
hydroxy;
an ether comprising a unit having the following formula:

-T¹-OR¹⁵ in which the T¹ and R¹⁵ are as defined hereinabove for Structure 1;

an ester comprising unit having either of the following formulas:

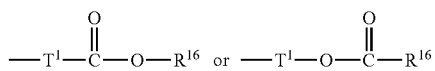

in which the T¹ and R¹⁶ are as defined hereinabove for Structure 1;

a carbonyl comprising unit having the following formula:

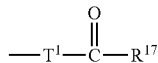

in which the T¹ and R¹⁷ are as defined hereinabove for Structure 1;

a nitrile comprising unit having the following formula:

-T¹-C≡N in which the T¹ is as defined hereinabove for Structure 1;

In the compounds having structure 8, it is preferred if the majority of X atoms are carbon and more preferred if n equals 2 and m equals 1 so that the cyclo structure is a substituted benzene derivative.

Examples of such molecules include 1,3,5-Trimethoxybenzene (621-23-8), Acetyl Eugenol (93-28-7), Acetyl Vanillin (881-68-5), Anisyl acetate (104-21-2), Methyl Eugenol (93-15-5), Musk thibetone (145-39-1), Musk ambrette (83-

66-9), 3,4-Dimethoxybenzoic acid (93-07-2), 3,4-Methylenedioxybenzyl acetate (326-61-4) and Veratraldehyde (120-14-9).

In the present specification, the following terms designate the name of the companies supplying the fragrance identified by commercial names: Firmenich=Firmenich SA; Takasago=Takasago International Corporation; Symrise=Symrise GmbH & Co. KG; Cognis=Cognis Corporation; Givaudan=Givaudan SA; IFF=International Flavors and Fragrances; Quest=Quest International; PFW=PFW Aroma Chemicals B.V.

It has been found that aldehydes not only react during the preparation of the but surprisingly they continue reacting over time on storage within the capsule itself to an extent which may make a fragrance olfactively unacceptable. Despite the general view that aldehydes are reactive species several aldehydes e.g. Lilial, Cyclamen aldehyde, hexyl and amyl cinnamic aldehydes and vanillin are frequently used at quite high levels in fragrances for household, laundry and personal care products. Thus perfume compositions of the present invention should preferably restrict the total level of fragrance aldehydes, including alpha, beta-unsaturated aldehydes, to less than 20% by weight, preferably less than 10% by weight, more preferably to less than 5% by weight, and even more preferably less than 1% by weight of the perfume composition.

Although it is known to add an excess of water soluble amines towards the end of capsule manufacture to reduce the formaldehyde concentration, we have found that amines present as core components show a surprising degree of reactivity.

Thus, perfume compositions of invention should preferably restrict the total level of primary and secondary amines to less than 10% by weight, and more preferably less than 1% by weight of the perfume composition.

Since the properties of the fragrance compounds no longer play a role in deposition, so the need to choose a proportion of high C log P (Calculated log P) materials as taught in U.S. Pat. Nos. 5,652,206 and 5,500,138 for improved delivery and fragrance longevity is no longer required, although it is still a requirement that the fragrance composition is sufficiently insoluble in water to form an emulsion. Since water solubility is approximately inversely correlated with C log P it is preferable that more than 80% by weight, preferably more than 90% by weight, of the fragrance composition comprises ingredients having C log P values greater than 1.00, more preferable is that more than 80% by weight and more preferably more than 90% by weight have C log P values greater than 1.50 and even more preferable is that more than 80% by weight and preferably more than 90% by weight have C log P values greater than 2.00.

As each capsule only contains a small quantity of fragrance, in order to achieve the maximum olfactive impact when the capsules release their contents, the fragrance materials of the encapsulated core should evaporate and diffuse through the air quickly and be olfactively strong. Materials which possess the correct balance of rapid evaporation and strength tend to have moderate C log P values. While the lower limit of C log P values is defined by the need to form a stable emulsion from water insoluble ingredients the upper limit is less sharply defined but still defined by the reducing rate of evaporation and perceived intensity brought about if the fragrance of the capsule core has a preponderance of high C log P ingredients. Thus it is preferred if most of the fragrance ingredients have C log Ps below 4.00. It is especially preferred if more than 40% by weight, preferably more than 60% by weight, and even more preferably that more than 80% by weight of the fragrance components of the capsule core have C log Ps less than 4.00 so as to deliver a strong fragrance when the capsules break and release their perfume.

C log P refers to the octanol/water partitioning coefficient (P) of fragrance ingredients. The octanol/water partitioning coefficient of a perfume ingredient is the ratio between its equilibrium concentrations in octanol and water. The partitioning coefficients of perfume ingredients are more conveniently given in the form of their logarithm to the base 10, log P. The log P of many perfume ingredients has been reported; for example, the Pomana 92 database, available from Daylight Chemical Information Systems, Inc. (Daylight CIS), Irvine, Calif., contains many, along with citations to the original literature. However, the C log P values reported herein are most conveniently calculated by the "CLOGP", program available within the Chemoffice Ultra Software version 9 available from CambridgeSoft Corporation, 100 Cambridge Park Drive, Cambridge, Mass. 02140 USA or CambridgeSoft Corporation, 8 Signet Court, Swanns Road, Cambridge CBS 8LA UK. The C log P values are preferably used instead of the experimental log P values in the selection of perfume ingredients which are useful in the present invention. For natural oils or extracts the composition of such oils can be determined by analysis or using the compositions published in the ESO 2000 database published by BACIS (Boelens Aroma Chemical Information Service, Groen van Prinsterlaan 21, 1272 GB Huizen, The Netherlands).

A further aspect of the invention is that the capsules should comprise more than 60% by weight, and more preferably more than 70% by weight, and even more preferably more than 80% by weight of perfumery ingredients and benefit agents. While it would seem obvious to incorporate as much active material as possible into the capsules, for many practical reasons associated with emulsion stability, capsule integrity, prevention of leakage etc., capsules often contain high proportions of other ingredients e.g. solvents, hardeners which substantially dilute the fragrance and benefit agents.

Since it is inherent in the success of this invention that more fragrance will deposited on surfaces and that the local concentration around ruptured capsules will be quite high, the composition of the capsule core must take account the less desirable characteristics of some fragrance materials such as persistence in the environment, accumulation in aquatic organisms, and toxic, allergenic or irritant effects with some humans.

In general, since the capsules will deliver fragrance more efficiently to the surface fewer capsules and hence less fragrance is needed to achieve a desired fragrance effect, so the overall environmental load is reduced. However the greater concentration on skin or in close proximity to the skin requires additional care to formulate the core composition using only ingredients known to be safe in such a context. Among the materials known to have undesirable characteristics and therefore excluded from the invention perfume compositions are nitro musks as exemplified by musk ambrette (CAS 83066-9), and musk ketone (CAS 8101401). Solvents especially the phthalate esters and carbitol ethers defined as $R-(OCH_2CH_2)_n-OR^1$ where n=1, 2 or 3 R=($C_1$ to $C_7$) alkyl or phenyl or alkyl substituted phenyl and $R^1$ is H or ($C_1$ to $C_7$) alkyl. Materials listed in Annex 1 of the Dangerous Substances Directive (67/548/EEC) or any of its amendments or ATPs (Adaptation to Technical Progress), or classified as R43 in their safety date sheet are optionally restricted to less than 1% of the core composition, preferably less than 0.1% by weight, more preferably below 0.001%, and even more preferably below the analytical detention limit.

It is also preferable if the levels of the following ingredients are limited to less than 25% by weight, preferably less than 10% by weight and more preferably less than 1% by weight of the core composition: Amyl cinnamic aldehyde (122-40-7), Amyl cinnamic alcohol (101-85-9), Anisyl alcohol (105-13-5), Benzyl alcohol (100-51-6), Benzyl benzoate (120-51-4), Benzyl cinnamate (103-41-3), Benzyl salicylate (118-58-1), Cinnamic aldehyde (104-55-2), Cinnamyl alcohol (104-54-1), Citronellal (106-22-9), Coumarin (91-64-5), Eugenol (97-53-0), Farnesol (4602-84-0), Geraniol (106-24-1) aldehyde (101-86-0), Hydroxycitronellal (107-95-5), Hydeoxymethylpentylcyclihexenecarbozaldehyde (31906-04-4), Isoeugenol (97-54-1), Lilial (80-54-6), Limonene (5989-27-5), Linalool (78-70-6), Methyl heptine carbonate (111-12-6), Methyl octane carbonate (111-80-8), Phenyl acetoaldehyde (122-78-1), 3-methyl-4-(2,6,6-trimethyl-2-cyclihexen-1-yl)-3-buten-2-one (127-51-5).

Optional Ingredients

Optionally other ingredients may be added to the capsule core or may be present as a consequence of the capsule preparation. These materials are not themselves fragrance materials but they may deliver other benefits such as antioxidants, sunscreen compounds, insect repellents etc, or they may be pro-fragrance molecules which react to release fragrance compounds, they may also include solvents, emulsifiers, stabilizers, polymers, and thickening agents.

Solvents

Olfactively weak or neutral solvents may constitute up to 25% of the capsule core material by weight, preferably less than 20% by weight, more preferably less than 10% by weight and even more preferably less than 5% by weight. If present they will most likely have been introduced with one or more perfume ingredients. In the perfume industry it is quite common to dissolve solid fragrance materials in a suitable solvent or to dilute powerful materials, used at low levels, with a solvent to facilitate manufacture. Typical solvents include high C log P materials such as Benzyl benzoate, Isopropyl myristate, Dialkyl adipates, Citrare esters such as acetyl triethyl cittate or acetyl tributyl citrate or triethyl citrate or Diethyl phthalate or low C log P materials such as Propylene glycol or Dipropylene glycol. While some of these materials could affect fragrance release from capsules during storage or emulsion properties during capsule manufacture, at the levels described such effects will be minimal. Moreover some solvents can be beneficial in certain products such as citrate esters being used to counter malodors in deodorants. Again, at the dosage levels described, these effects should be minimal. Thus solvents are considered as part of the fragrance but not necessarily compliant with the invention rather than as a benefit agent.

Pro-Fragrances

Another optional ingredient which it may be desirable to protect within and deliver from a microcapsule is a pro-fragrance. Pro-fragrance are compounds in which small usually highly volatile fragrance are reacted to form higher molecular weight molecules but which are designed to release the fragrance molecule due to some external event such as a pH change, or by exposure to sunlight, or due to the molecule having a particularly labile bond which can hydrolysis to release the fragrance molecule. Pro-fragrances generally have a molecular weight of at least 300 amu, preferably greater than 350 amu, more preferably greater than 400 amu and that the molecular weight of pro-fragrance is at least 2 times, preferably at least 2.5 times, more preferably 3 times the molecular weight of the fragrance material component and must release more than one molecule of fragrance per molecule of pro-fragrance. Moreover the released fragrance material must have a molecular weight of between 100 and 300 amu, preferably between 100 and 250 amu and an odor detection threshold below 100 ppb preferably 10 ppb as defined in U.S. Pat. No. 6,077,821 incorporated herein by reference. Pro-fragrance are often acetals, ketals, schiff bases, labile esters such as ortho esters, carbonate esters, silyl esters or carboxylic acid esters activated by neighbouring functional groups. The following patents or patent applications describe various pro-fragrance molecules and their use in household and personal care products and are incorporated herein by reference: U.S. Pat. No. 6,551,987 and U.S. Pat. No. 6,077,821. More than one pro-fragrance may be incorporated within the core of a capsule. Thus pro-fragrances need not comply with the molecular weight requirements of fragrance molecules but they must comply with the other structural constraints listed as a) to g).

Other Benefit Agents

In the context of this specification, other benefit agents means any material capable of being encapsulated in the way described later and which can survive storage to deliver a benefit when used in liquid, gel, paste or soft solid household, laundry, personal care or cosmetic products, provided they contains little or none of any aldehydic compounds, including alpha beta unsaturated aldehydes, or primary or secondary amines, and meet the structural requirements of the invention for bulky molecules as defined for fragrance ingredients of the invention. Benefit agents do not necessarily rely upon volatility for their effect so they need not be constrained by molecular weight but to minimize leaching from the shell during storage they need to conform with the structural requirements of bulky molecules.

Benefit agents include natural extracts or materials which have therapeutic effects as relaxants or stimulants, e.g. 1,3,5-trimethoxybenzene (621-23-8), 1,3-dimethoxy-5-methylbenzene, or vitamins or vitamin derivatives such as tocopheryl acetate (58-95-7) or retinyl palmitate (79081-2) are also benefit agents within this definition. Materials which suppress or reduce malodor and its perception by any of the many mechanisms proposed are benefit agents as described in U.S. Pat. No. 4,622,221 and U.S. Pat. No. 4,719,195. Materials which when added to the emulsion improve the properties of the core emulsion before encapsulation, or the properties of the capsules themselves. Materials which provide a warming or cooling effect such as described in Cosmetics and Toiletries Vol. 120 No. 5 p. 105 by M Erman are also benefit agents, Examples of such agents include but are not limited to: Cyclohexane carboxamide N-Ethyl-5-methyl-2-(1-methylethyl) known as cooling as WS3™ (39711-79-0); Menthyl lactate (59259-38-0); (−)-Menthoxypropane-1,2-diol known as cooling agent 10™. Materials which act as insect repellents p-Menthane-3,8-diol (42822-86-6) or natural plant oils such as Tea Tree oil, Neem oil, or Eucalyptus oil are benefit agents. Materials which act as antioxidants such as Butylated hydroxy toluene (128-37-0), or Butylated hydroxyanisole (25013-16-5), or Pentaerythrityl tetra-di-t-butyl hydroxyhydrocinnnamate, Ocradecyl di t-butyl-4-hydroxyhydrocinnamate (2082-79-3), Tetrabutyl ethylidenbisphenol (35958-30-6) are benefit agents. Materials which act as UV absorbers such as Benzophenone, Butylmethoxydibenzoylmethane, or Tetrakis-[methylene-3-(3',5'-di-tert-butyl-4'-hydroxyphenyl)propionate]methane (6683-19-8), bis-ethylhexyloxyphenol-methoxyphenyl-triazine are benefit agents. The materials listed above are intended to exemplify the benefit agents but are not intended to limit the benefit agents to this list. Mixtures of the above may also be considered as benefit agents of the invention. Thus it may be advantageous to combine UV absorbers with antioxidants to protect the fragrance ingredients. Moreover it is recognized that some materials may exhibit more than one benefit. Thus vitamin E acetate can function as an antioxidant as well as a vitamin precursor.

Core Shell Capsules

The invention can be applied to any core shell capsule which comprises a central core of perfume surrounded by a polymeric layer which forms the wall or shell layer. The word shell may give the impression of a hard walled capsule but this need not necessarily be so, it indicates no more than a covering layer which protects the contents but the shell may be plastic and deformable. Capsules of the invention are typically 1-1000 micrometers in diameter, preferably 5-500 µm and more preferably 10-100 µm.

Co-Acervates

One form of microcapsule can be those typically formed by coacervation techniques. The materials and processes are described in detail in the following patents incorporated herein by reference, e.g., U.S. Pat. No. 2,800,458; U.S. Pat. No. 3,159,585; U.S. Pat. No. 3,533,958; U.S. Pat. No. 3,697, 437; U.S. Pat. No. 3,888,689; U.S. Pat. No. 3,996,156; U.S. Pat. No. 3,965,033; U.S. Pat. No. 4,010,038; and U.S. Pat. No. 4,016,098. Preferred encapsulating material is gelatin coacervated with a polyanion such as gum Arabic and more preferably cross-linked with a cross-linked material such as glutaraldehyde or alginates co-acervated with calcium ions.

Aminoplast Capsules

An especially preferred form of microcapsules is an aminoplast capsule formed by condensation polymerization of amines and aldehydes preferably melamine formaldehyde and optionally urea. Patents describing compositions and processes for manufacturing aminoplast capsules in the form of a dispersion such as EP patent application 1,246,693 A1 and U.S. Pat. No. 6,261,483 which are incorporated herein by reference. Other suitable monomers for core shell capsules are for example methyl methacrylate as exemplified in international patent application WO0149817, and urethanes as exemplified in international patent application WO03099005. Additional suitable monomers are well known to those skilled the art of polymerization reactions. Without wishing to limit the patent in any way a typical process for preparing a capering a capsule dispersion would include the following steps.

The preparation of an emulsion of the perfume ingredients and any benefit agent or modifiers which may include emulsifying agents or emulsion stabilizers takes place under vigorous agitation.

The first step is the addition of fragrance oil, methylated melamine-formaldehyde resin (with a melamine:formaldehyde:methanol mixture in the approximate molar ratios 1:3:2 to 1:6:4) and an emulsifier. These monomers may be precondensed or the monomers may be used directly. Soma of the melamine can be replaced by urea.

Acid is added to adjust to a pH of 3.5 to 6.5 and the temperature raised to 30-45° C. Agitation is allowed to proceed until the dispersion is oil free. Any acid which has no adverse properties may be used in this process, such as for example formic acid or acetic acid.

It is particularly advantageous if the capsules are cured by heating to a temperature between 60° C. to 100° C. for several hours under moderate agitation.

It is particularly advantageous if during the early phase of coring a further addition of urea, melamine or other amines, or mixtures thereof can be made to reduce the formaldehyde concentration in the finished dispersion, and increase the wall thickness. Typically 10-30% additional melamine and/or urea can be added at this stage, and a particularly advantageous ration is 5:1 to 1:1 melamine:urea.

Once curing is complete, the temperature is reduced to around 50° C., and the dispersion is neutralized before being adjusted to a pH around 9.5

For ease of handing when introducing capsules into liquid products, it is preferable to add a dispersing agent to the slurry to prevent the capsules sedimenting or creaming which may form large aggregates which can be difficult to redistribute.

The final capsule dispersion as shipped should preferably contain less than 0.1% by weight of free formaldehyde measured by GLC, preferably less than 100 ppm (wt/wt) and more preferably less than 10 ppm (wt/wt).

It may also be advantageous to incorporate physically or chemically further materials to improve capsule deposition to substrates or to improve deposition selectivity during application. Such materials as cationic polymers or copolymers e.g., polyvinyl imidazole, polysaccharides based on beta 1,4 linkages such a guar gum, and polyester copolymers such as those sold commercially as soil release polymers for detergents.

Capsules of the above process will generally have a particle size within the range from 5-100 µm depending on the emulsifying conditions. The capsule wall will have a thickness of 0.025-1.0 µm. These parameters are preferable for the proper functioning of the capsules of this invention. If the capsule wall is too thin, the capsules will be too friable for subsequent shipping and handling, if too thick they might not break when required. If capsules are very small the wall material may become an uneconomically large proportion of the capsule. Very large capsules either require thicker malls or the addition of hardeners to the core to prevent breakage in handing both of which reduces the amount of beneficial agent delivered.

The final dispersion may typically contain from 2.5%-80%, preferably 10%-70% and more preferably 20%-70% capsules dispersed in water. In some forms of the process excess water can be removed to from ether a concentrated wet cake or a dry free flowing powder as best suits the subsequent application.

Household Laundry and Personal Care Compositions

The formulations and ingredients of household, laundry and personal care products and cosmetics in which capsules containing fragrance compositions of the invention may be used are well known to those skilled in the art, reference may be made to the following works which are incorporated herein reference:

Formulating Detergents and Personal Core Products A guide to Product Development by L Ho Tan Tai, ISBN 1-893997-10-3 published by the AOCS Press. Also to Volume 67 of the Surfactant Science Series Liquid Detergents ISBN 0-8247-9391-9 (Marcel Dekker Inc.), as well as to the following patents or patent applications:

Fabric Softeners and Conditioners:
U.S. Pat. Nos. 6,335,315; 5,674,832; 5,759,990; 5,877,145 and 5,574,179;

Liquid Laundry Detergents:
U.S. Pat. Nos. 5,929,022; 5,916,862; 5,731,278; 5,470, 507; 5,466,802; 5,460,752 and 5,458,810;

Shampoos and Hair Conditioners:
U.S. Pat. Nos. 6,162,423; 5,968,286; 5,935,561; 5,932, 203; 5,937,661; 5,776,443; 5,756,436; 5,661,118 and 5,618, 523.

The tendency of fragrance materials to leak from capsules will be influenced by the product composition. High levels of surfactant might be expected to increase the rate escape whilst lower levels of surfactant would not assist solubilisation. Other factors such as product viscosity and product pH might also affect the rate of release by influencing the molecules mobility or by ionizing chemical groups such as amines in the shell wall. The effect of differing product compositions on leakage is observed in the examples. Ultimately products have to perform in commercial formulations but for ease of testing and for comparison into the future we have defined a buffered surfactant solution as the standard conditions for a storage test. Capsules to give 0.5 g by weight of encapsulated fragrance were gently mixed into 10 g of a 10% by weight solution of sodium dodecyl sulfate in demineralised water buffered to pH 8.5 with a citrate phosphate buffer and stored in a sealed glass bottle at 40° C. The free fragrance was determined by headspace GCMS at the start of the experiment and again after 4 weeks. A control sample was prepared from 0.5 g of the fragrance used in the encapsulation, dissolved in a 10% by weight solution of sodium dodecyl sulfate in demineralised water buffered to pH 8.5 with a citrate phosphate buffer and stored in a sealed glass bottle at 40° C. Comparing area counts from the headspace measurements at time zero indicates the extent of any fragrance ingredients which were not encapsulated, or which the extent of greater than 50% and more preferably greater than 75% of the control sample after 4 weeks storage at 40° C.

On incorporating capsules into liquid products there is a tendency for the capsules to "cream" i.e. rise to the surface, or to "sediment" i.e. to settle, on extended storage over a normal temperature range (4° C.-40° C.) due to differences in density between the liquid and the capsules. While many factors affect the rate at which the creaming or sedimenting occurs it is helpful if the products themselves slow or prevent separation. For example if the products have high viscosities at very low shear rates the capsules will tend to remain evenly distributed throughout the product. Hence it is preferable if the products into which capsules are introduced have viscosities of greater than 100 mPas preferably greater than 1000 mPas measured at a shear rate of 5 $s^{-1}$ using a Brookfield LVT viscometer.

The present invention will be now disclosed in more details by the following illustrative, but not limiting, examples.

Example 1

Preparation of Capsules

A 2 liter cylindrical stirring vessel was fitted with an infinitely adjustable disperser having a standard commercial dispersion disk with a diameter of 50 mm.
It was charged in succession with:
400 g of Fragrance oil;
86 g of a 70% strength aqueous solution of a methylated melamine-formaldehyde resin (molar ration melamine:formaldehyde:methanol, 1:3.9:2.4) with a viscosity of 275 mPa·s and a pH of 8.5;
80 g of 20% strength solution of poly-2-acrylamide-2-methylpropanesulfonic acid sodium salt;
350 g of water;
15 g of 10% strength by weight aqueous formic acid solution.

This charge was processes to a capsule dispersion by adjusting the stirring speed to a peripheral speed of approximately 20 mps. The temperature was held at about 35° C.

After 60 minutes, the dispersion was oil-free; a particle size of about 20-30 μm had been established. The stirring speed of the dispersion disk was then reduced to a level sufficient for uniform circulation of the vessel contents.

A cure temperature of 80° C. was set, and once reached by injection of hot steam, a feed of a 27% suspension of melamine-urea (ratio 2.5:1, melamine:urea) in formic acid (to adjust pH to pH 4.5) was added to the dispersion of the preformed microcapsules with a contact mass flow rate and was metered in over the course of an hour. A total of 46 g of the suspension of melamine-urea was metered in.

A cure phase of 120 min ensues at 90° C.

After the dispersion had been cooled to about 55° C., it was neutralized with diethanolamine to pH 7.0 and adjusted to a pH of 8.5 using ammonia.

A dispersing agent was added to give a uniform capsule dispersion with a solids content of 50% and a viscosity of 83 mPa·s.

Example 2

Comparison of Ingredient Leakage

Table 1 compares the leakage of individual fragrance components from a fragrance encapsulated, using the method of example 1, with the capsules dosed at the equivalent of 0.5% of fragrance into a range of liquid laundry and personal care products. The results are quoted as percentage fragrance released compared with the equivalent amount of free fragrance dosed into the same product as a control. Some of the fragrance ingredients meet the criteria for bulky molecules of the invention, while other comparative examples such as Acetophenone, Eugenol, Benzyl acetate, and Ethyl Benzoate do not meet these criteria. Ingredient concentration was measured by GCMS after SPME headspace capsule of the volatiles in the headspace after storage at 40° C. for 4 weeks.

TABLE 1

| Compound (CAS No.) | Clog P | Persil Sens[1] | Lenor Conc[2] | Dash Reg[3] | Via Sens[4] | Downy[5] | Tide Free[6] | Sampoo[7] |
|---|---|---|---|---|---|---|---|---|
| 1,4-Cineol (470-67-7) | 2.81 | 1 | 29 | 15 | 10 | 8 | 13 | 2 |
| Eucalyptol (470-82-6) | 2.83 | 2 | 36 | 16 | 2 | 2 | 12 | 13 |
| Borneol (464-45-9) | 3.09 | <1 | 23 | 8 | 3 | 3 | 4 | 2 |
| Ethyl Benzoate (93-89-0) | 2.64 | 91 | 48 | 100 | 100 | 100 | 97 | 100 |
| Buccoxime (75147-23-8) | 2.55 | <1 | — | 3 | 3 | — | 3 | <1 |
| Cedanol (7070-15-7) | 3.12 | <1 | 3 | <1 | <1 | 3 | 1 | 1 |
| Fruitate (80657-64-3) | 3.37 | <1 | <1 | <1 | <1 | <1 | <1 | <1 |
| β-Ionone (14901-07-6) | 3.71 | <1 | 12 | — | <1 | <1 | 1 | 1 |
| Spirambrene (121251-67-0) | 4.63 | <1 | <1 | — | <1 | <1 | <1 | <1 |
| Eugenol (97-53-0) | 2.40 | 45 | 100 | 96 | 93 | 100 | 79 | 88 |
| Galaxolide (1222-05-5) | 5.74 | <1 | <1 | <1 | <1 | <1 | <1 | <1 |
| Ethylene Brassylate (105-95-3) | 2.46 | <1 | 25 | — | 28 | 60 | <1 | 39 |
| Acetophenone (98-86-2) | 1.58 | 92 | 42 | 95 | 61 | 72 | 73 | 84 |
| Benzyl acetate (140-11-4) | 1.96 | 86 | — | 87 | — | 81 | 63 | 100 |
| Para-tertiary-butyl-Cyclohexanone (98-53-3) | 2.71 | 10 | — | 33 | 34 | 41 | 14 | 2 |

TABLE 1-continued

| Compound (CAS No.) | Clog P | Persil Sens[1] | Lenor Conc[2] | Dash Reg[3] | Via Sens[4] | Downy[5] | Tide Free[6] | Sampoo[7] |
|---|---|---|---|---|---|---|---|---|
| Dimethylbenzylcarbinyl Acetate (151-05-3) | 3.30 | 4 | — | 44 | 11 | 12 | 18 | <1 |
| α-Damascene (24720-09-0) | 3.82 | <1 | 9 | 16 | <1 | <1 | 1 | <1 |
| Cyclacet (5913-60-5) | 2.87 | 21 | — | — | 17 | 18 | 25 | <1 |
| Vigoflor (68480-11-5) | 3.14 | 1 | 31 | 6 | 4 | 3 | 6 | <1 |
| Cashmeran (33704-61-9) | 4.00 | <1 | 1 | <1 | <1 | <1 | <1 | <1 |
| Iso butylquinoline (65442-31-1) | 3.98 | <1 | — | 9 | 5 | 17 | 11 | <1 |
| Rhubofix (41816-03-9) | 3.46 | <1 | — | <1 | <1 | <1 | <1 | <1 |

— indicates not measured
Buccoxime is 1,5-Dimethyl-bicyclo[3,2,1]octan-8-one oxime (Supplied by Symrise);
Cedanol is 2-Isobornyloxyethanol (Supplied by Takasago);
Fruitate is Ethyl tricyclo[5,2,1,0]decan-2-carboxylate (Supplied by Kao);
Spirambrene is 2,2,3',7',7'-Pentamethylspiro(1,3-dioxan-5,2-nocarane) deastereoisomers (Supplied by Givaudan SA);
Galaxolide is 1,2,3,4,6,7,8-Hexahydro-4,6,6,7,8,8-hexamethylcyclopenta-γ-2-benzopyran (Supplied by International Flavors and Fragrances);
Cyclacet is Tricyclodecenylacteate (Supplied by International Flavors and Fragrances);
Vigoflor is Decahydrospiro(fran-2(3H),5'-(4,7)menthano(5H)indene (Supplied by International Flavors and Fragrances);
Cashmeran is 6,7-Hihydro-1,1,2,3,3-pentamethyl-4(% H)-indanone (Supplied by International Flavors and Fragrances);
Rhubofix is 3',7'-Hexahydrodimethylspiromethanonaphthalene (Supplied by Firmenich SA).

The commercial products used in the test are as follows eith product name, supplier and country of origin.
1. Persil Sensitive concentrated liquid detergent from Henkel in Germany;
2. Lenor Concentrate from Procter and Gamble in the UK;
3. Dash Regular liquid detergent from Procter and Gamble Italy;
4. Via Sensitive concentrated liquid detergent from Lever Faberge Sweden;
5. Ultra Downy Procter and gamble USA;
6. Tide Perfume and Dye Free from Procter and Gamble USA;
7. Shampoo Schauma from Henkel Germany.

While there is some variation in perfume escape from the capsules in different product formulations, it is clear that fragrance ingredients of the invention do not escape at the same rate as the control ingredients. Particular attention should be paid to the difference in results between Eugenol and Ethylen Brassylate which have similar C log P values but different release rates in the products.

Example 3

TABLE 2

| Compound (CAS No.) | Clog P | Persil Sens[1] | Lenor Conc[2] | Via Sens[4] | Downy[5] | Tide Free[6] | Sampoo[7] |
|---|---|---|---|---|---|---|---|
| Vertenex (32210-23-4) | 4.06 | 0 | 21 | 0 | 0 | 0 | 0 |
| Spirambrene (121251-67-0/ 121351-68-1) | 4.63 | 0 | 0 | 0 | 0 | 0 | 0 |
| Limonene (5989-27-5) | 4.35 | 16 | 60 | 28 | 44 | 31 | 15 |
| Citronelly nitrile (51566-62-2) | 3.09 | 15 | 47 | 73 | 67 | 82 | 3 |
| 1,4-Cineole (470-67-7) | 2.81 | 1 | 29 | 10 | 8 | 13 | 2 |

Vertenex is Para-tertiary-butylcyclohexyl acetate (Supplied by International Flavors and Fragrances);
Spirambrene is 2,2,3',7',7'-Pentamethylspiro-(1,3-dioxan-5,2'-norcarane) (Supplied by Givaudan SA).

Table 2 again shows same variation in escape due to the differences among the products but compounds of the invention such as Vertenex and 1,4-Cinaole are better retained while less water soluble materials, i.e. with higher C log P values, such as limonene, are not so well retained in the capsule.

Example 4

A fragrance composition is shown in table 3 having a note suitable for use in household laundry and personal care products exemplifying the invention with 26% by weight of the ingredients conforming to the invention.

TABLE 3

| Name | Supplier | CAS | Wt % |
|---|---|---|---|
| Ambrinol 20T | Takasago | 41199-19-3 | 4.0 |
| Borneol | | 464-45-9 | 2.0 |
| Cedanol | Takasago | 7070-15-7 | 4.0 |
| α-Damascone | | 24720-09-0 | 4.0 |
| Ethylene Brassylate | Takasago | 105-95-3 | 10 |
| Fruitate | Kao | 80657-64-3/ 80623-07-0 | 2.0 |
| Total ingredients of the invention | | | 26.0% |
| Allyl cyclohexyl propionate | | 2705-87-5 | 17.5 |
| Dihydromyrcenol | | 18479-58-8 | 35 |
| Styrally acetate | | 93-92-5 | 17.5 |
| Cyclogalbanate | | 68901-15-5 | 4 |

Example 5

A fragrance composition is shown in table 4 having a fruity note suitable for use in household and personal care products, exemplifying the invention with 43.5% by weight of the ingredients conforming to the invention.

TABLE 4

| Name | Supplier | CAS | Wt % |
|---|---|---|---|
| Aphermate | IFF | 25225-08-5 | 1.5 |
| Fruitate | Kao | 80657-64-3/ 80623-07-0 | 4.5 |
| Ethylene Brassylate | Takasago | 105-95-3 | 10.0 |
| Trilal | IFF | 68039-49-6 | 5.0 |
| Verdox | IFF | 88-41-5 | 20.0 |
| β-Ionone | IFF | 14901-07-6 | 2.0 |
| Dimethyl benzyl carbinyl acetate | | 151-05-3 | 0.5 |
| Total ingredients of the invention | | | 43.5% |
| Cis-3-hexenyl acetate | | 3681-71-8 | 4 |
| Hexyl acetate | | 142-92-7 | 10 |
| Allyl heptanoate | | 142-29-8 | 16.0 |
| α-terpineol | | 98-55-5 | 26.5 |

Example 6

A fragrance composition is shown in table 5 having a note suitable for use in household and personal care products, exemplifying the invention with 60% by weight of the ingredients conforming to the invention.

TABLE 5

| Name | Supplier | CAS | Wt % |
|---|---|---|---|
| Ethylene Brassylate | Takasago | 105-95-3 | 10 |
| Verdox | IFF | 88-41-5 | 10 |
| β-Ionone | IFF | 14901-07-6 | 5.0 |
| 1,3,5-Trimethoxybenzene | | | 35 |
| Total ingredients of the invention | | | 60% |
| Linalyl acetate | | 115-95-7 | 20 |
| Linalool | | 78-70-6 | 20 |

Example 7

A fragrance composition is shown in table 6 having a citrus note suitable for use in household and personal care products, exemplifying the invention with 83% by weight of the ingredients conforming to the invention.

TABLE 6

| Name | Supplier | CAS | Wt % |
|---|---|---|---|
| Eucalyptol | | 470-82-6 | 5.0 |
| Iso bornyl acetate | | 125-12-2 | 12.0 |
| Diphenyl oxide | | 101-84-8 | 10.0 |
| Bornyl acetate | | 5655-61-8 | 5.0 |
| β-Ionone | IFF | 14901-07-6 | 10 |
| Fruitate | Kao | 80657-64-3/ 80623-07-0 | 3.0 |
| Verdox | IFF | 88-41-5 | 8.0 |
| Dimethyl benzyl carbinyl acetate | | 151-05-3 | 5.0 |
| Ethylene Brassylate | Takasago | 105-95-3 | 25.0 |
| Total ingredients of the invention | | | 83% |
| Orange oil | | Natural oil | 12.0 |
| Dihydromyrcenol | | 18479-58-8 | 5.0 |

Example 8

Standard liquid detergents (St Liq 1 to 4) or concentrated liquid detergents (Conc Liq 1 to 4) containing fragrance capsules of the invention.

TABLE 7 liquid Laundry Detergent Compositions

| INGREDIENT | St Liq 1 Wt % | St Liq 2 Wt % | St Liq 3 Wt % | St Liq 4 Wt % | Conc Liq 1 Wt % | Conc Liq 2 Wt % | Conc Liq 3 Wt % | Conc Liq 4 Wt % |
|---|---|---|---|---|---|---|---|---|
| NA-LAS | 9.5 | | | | 14 | | | |
| NA-PAS | | 4 | 10 | 7 | 4 | 5 | 5 | 15 |
| NA-AES | | | 2 | 2 | | | | 2.6 |
| NONIONIC 7EO | 15 | 9 | 3.5 | 4.5 | 15 | 24 | 22 | 5 |
| CATIONIC | | | 1 | | | | | 2 |
| SOAP | 15 | 15 | 7 | 6 | 12 | 17 | 18 | 11 |
| APG | | 4 | | | | 4 | 2.5 | |
| GLUCOSAMIDE | | | 4.5 | 4 | | | | 6 |
| MONO ETHANOLAMINE | | | 5 | 3.5 | | | | 6.5 |
| CITRATE | 1 | 1 | 2 | 1.2 | 6 | 1 | 4 | 2 |
| PROPYLENE GLYCOL | | 3 | 6 | 6 | 5 | | 3 | 8 |
| GLYCEROL | | | | | | 4 | | |
| ETHANOL/IMS (INDUSTRIAL ALCOHOLS) | 7 | 2 | 1 | 1 | | 7 | 1.5 | 2.2 |
| PERFUME | 0.3 | 0.2 | 0.2 | 0.0 | 0.5 | 0.5 | 0.4 | 0.0 |
| ENCAPSULATED PERFUME OF EXAMPLE 4 | | 0.2 | | | | | 0.3 | |
| ENCAPSULATED PERFUME OF EXAMPLE 5 | | | 0.3 | | | 0.2 | | |
| ENCAPSULATED PERFUME OF EXAMPLE 7 | 0.1 | | | | 0.1 | | | |
| VISCOSITY MODIFIER | 0.25 | | 0.25 | 0.25 | 0.18 | | | 0.18 |
| ANTI-FORMING AGENT (15% MA) | 1 | 0.7 | 0.7 | 0.7 | 1 | 1 | 1 | 1 |
| FLUORESCENT AGENT (15% MA) | 1.1 | 0.7 | 0.7 | 0.7 | 1 | 1 | 1 | 1 |
| DEFLOCULATING AND SEQUESTRATING AGENT (DEQUEST ® 2040 AND 2010) | 1 | 1 | 1.4 | 1 | 1.5 | 1.5 | 1.5 | 1.5 |

TABLE 7-continued liquid Laundry Detergent Compositions

| INGREDIENT | St Liq 1 Wt % | St Liq 2 Wt % | St Liq 3 Wt % | St Liq 4 Wt % | Conc Liq 1 Wt % | Conc Liq 2 Wt % | Conc Liq 3 Wt % | Conc Liq 4 Wt % |
|---|---|---|---|---|---|---|---|---|
| ENZYMES (PROTEASE, LIPASE, CELLULASR, AMYLASA) | 0.7 | 1.05 | 1.05 | 0.9 | 1.2 | 1.2 | 1.2 | 1.2 |
| POLYMERS FOR FABRIC MAINTENANCE) ELIMINATION OF STAINS DYE TRANSFER ETC | 1 | 1 | 1 | 1 | 1.5 | 1.5 | 1.5 | 1.5 |
| WATER | 47.05 | 57.15 | 52.40 | 59.85 | 37.02 | 21.1 | 37.1 | 32.62 |
| TOTAL | 100 | 100 | 100 | 100 | 100 | 100 | 100 | 100 |

NA-LAS: Sodium salt of linear alkyl benzene sulfonate with $C_{11}$-$C_{15}$ chain length
NA-PAS: Sodium salt of alkyl sulfate, the sulfate ester of a commercial primary alcohol with alkyl chains in the range $C_{12}$-$C_{20}$
NA-AES: Sodium salt of an alkyl ether sulfate in which an alcohol has been etherified with ethylene oxide prior to making the sulfate ester
Nonionic 7EO: linear long chain primary alcohols condensed with an average of 7 moles of ethylene oxide
Cationic: a quaternary ammonium salt $RN+(CH_3)(CH_2H_4OH)$ with R being a long alkyl chain in the range $C_8$-$C_{14}$ carbon units
Soap: Sodium linear alkyl carboxylates derived from a mixture of long alkyl chain fatty acid such as tallow, palm, or coconut fatty acids
APG: $C_{10}$-$C_{18}$ alkyl chain polyglycoside surfactants Example 9

Standard Softener (St FC 1-2) or Concentrated liquid softener (Conc FC 1-2) exemplifying the invention by incorporation capsules of examples 4 and 5.

TABLE 8

Liquid Fabric Conditioner Compositions

| INGREDIENT | St FC 1 Wt % | St FC 2 Wt % | Conc FC 1 Wt % | Conc FC 2 Wt % |
|---|---|---|---|---|
| TETRANYLAHT-1 | 5.0 | | 12.0 | |
| DEQA | | 7.0 | | 18 |
| GENAPOL C200 | 0.1 | | 0.75 | 3 |
| ISOPROPYL ALCOHOL | | 2.0 | | 3 |
| POLYETHYLENE GLYCOL 4000 | | | | 0.6 |
| LAUREX CS | 0.4 | | 1.8 | |
| PERFUME | 0.2 | 0.25 | 0.5 | 0.35 |
| ENCAPSULATED PERFUME OF EXAMPLE 4 | 0.1 | | | 0.35 |
| ENCAPSULATED PERFUME OF EXAMPLE 5 | | 0.2 | 0.3 | |
| CALCIUM OR MAGNESIUM CHLORIDE | | | | qs |
| DYE, ANTUFOAMING AGENT, PRESERVATIVE | qs | qs | qs | qs |
| WATER QSP | 100 | 100 | 100 | 100 |

Tetranyl AHT-1; semi-hard tallow ester of triethanolammonium methosulfate, marketed by Kao Corp.
Genapol C200; copra ethoxylate, marketed by Clariant
Laurel CS; Long chain alcohol, marketed by Albright & Wilson
DEQA; soft di(tallow oxyethyl)dimethylammonium chloride Example 10

A Hair Shampoo formulation containing perfume capsules of examples 5 and 6.

TABLE 9

A Shampoo Formulation

| Ingredient | Wt % | Wt % | |
|---|---|---|---|
| Lauryl Ether Sulfate | 14.0 | 14.0 | Texapon N70 ex (Cognis) |
| Cocoamidepropyl betaine | 6.5 | 6.5 | DehytonAB30 ex (Cognis) |
| Glycerol | 2.0 | 2.0 | |
| Sodium N-cocoylamidoethyl N-ethoxycarboxymethylglycinate | 2/0 | 2/0 | Miranol 2CM ex (Rhodia) |
| Coconut Monoethanolamide | 0.8 | 0.8 | Comperlan 100 ex (Cognis) |
| Copolymer of dimethyl ammonium chloride and acrylamide | 1.5 | 1.5 | Merquat S ex (Nalco) |
| Copolymer of acrylic acid and atearyl methacrylate | 0.3 | 0.3 | Carnopol 1382 ex (Noveon) |
| Salicylic Acid | 0.2 | 0.2 | |
| Sodium Benzoate | 0.5 | 0.5 | |
| Disocdium Ethylene diamine tetraacetate | 0.25 | 0.25 | Dissolvine Na-2 ex(Akzo Nobel) |
| Perfume | 0.2 | 0.2 | |
| Encapsulated Perfume of Example 5 | 0.2 | | |
| Encapsulated Perfume of Example 6 | | 0.2 | |
| Ethylene glycol distearate | 0.2 | 0.2 | EginBL315 ex (Goldschmidt) |
| PH adjust with citric acid solurion or Sodium hydroxide solution | To pH 5.2 | To pH 5.2 | |
| Water | To 100 | To 100 | |

While the present invention has been described in detail and with reference to specific embodiments thereof, it will be apparent to one skilled in the art that various changes and modifications can be made therein without departing from the scope thereof.

This application is based on European patent application No. 06 300 921.1 filed Sep. 4, 2006, the entire contents thereof being hereby incorporated by reference.

Further, all the documents cited herein are incorporated by reference.

What is claimed is:

1. A fragrance composition to be incorporated into the core of a core shell capsule, comprising:

I) 60-100% by weight of at least 5 different fragrance compounds, each of the at least 5 different fragrance compounds possessing any of the following structural features a) to g), and
II) 0-40% by weight of other benefit agents which possess any of the following structural features a) to g), pro-fragrances, and solvents:
a) a fragrance compound containing more than one ring, each ring having between 3 and 8 atoms of any of carbon, oxygen, nitrogen or sulfur in any ring and no atoms being shared by any of the rings, and selected from the group consisting of methyl n-{4-(4-hydroxy-4-methylpentyl)-3-cyclohexen-1-methylene}-anthranilate, endo 4-(5-methyl1-5-norbornen-2-yl)-pyridine, 2,5,5-trimethyl-2-phenyl1,3-dioxane, isocamphyl cyclohexanol, 2-(2,4-dimethyl-3-cyclohexyl)-5-methyl-5-(1-methylpropyl)-1,3-dioxane, vanillin propylene glycol acetal, indol-hydroxycitronellal schiff's base, dimethyl-2-(5',5', 8',8'-tetramethyl-5',6',7',8'-tetrahydro-naphthalen-2'-yl) 1,3-dioxolane, 2 cyclohexylidene-2-phenylacetonitrile, benzyl cinnamate, benzyl eugenol, cinnamyl anthranilate, cinnamyl cinnamate, cinnamyl phenyl acetate, 4-methyl-2-phenyltetrahydro-2h-pyran, and dibenzyl ketone;
b) a fragrance compound having at least two rings, each ring having between 3 and 8 atoms of any of carbon, oxygen, nitrogen or sulfur in which any rings share one common atom, and selected from the group consisting of 2-methyl-1,5-dioxaspiro[5.5]undecane, 2,2,3',7',7'-pentamethylspiro(1,3-dioxan-5,2'-norcarane), decahydrospiro[furan-2(3h), 5'-(4,7-methano-5h-indene)], 3,3-dimethyl-1,5-dioxaspiro[5.5]undecane, 4-methyl-1-oxaspiro[5.5]undecene, and 8-methyl-1-oxaspiro[4.5] decan-2-one;
c) a fragrance compound having at least two rings, each ring having between 3 and 8 atoms of any carbon, oxygen, nitrogen or sulfur in which any two rings share at least two adjacent common atoms, and selected from the group consisting of methyl naphthyl ketone, isobutylquinoline, 6,7-dihydro-1,1,2,3,3-pentamethyl-4(5h)-indanone, tricyclo decenyl acetate and its homologues tricyclo decenyl propionate and tricyclo decenyl isobutyrate, cedryl methyl ether, 4-(1,3-benzodioxol-5-yl)butan-2-one, 3a-ethyl dodecahydro-6,6,9a-trimethyl naphtho[2,1-b]-furan, 2,5,5-trimethyl-octahydronaphthalen-2-ol, α-cedrene, 8-cedren-13-ol, cedryl methyl ether, α-methyl-3,4-methylenedioxy hydrocinnamic aldehyde, ethyl tricyclo[5,2,1,0]decan-2-carboxylate, 1,4-cineole (470-67-7), 1,8-cineole, borneol, bornyl acetate, isoborneol, isobornyl acetate, isobornyl formate, isobornyl methyl ether, isobornyl propionate, 2-ethyl-5(or 6)-methoxy bicyclo[2.2.1]heptane and 1-ethyl-3-methoxy tricyclo[2.2.1.0$^{2,6}$]heptane, 2-ethylidene-6-isopropoxy bicyclo[2.2.1]heptane, 5' (or 6')-(methylnorborn-5'-en-2'-yl)-2-menthyl-1-en-3-ol, 2-[(1,7,7-trimethybicyclo[2,2,1]hept-2-yl)oxy]-ethanol, 7 acetyl-1,2,3,4,5,6,7,8-octahydro-1,1,6,7-tetramethyl-naphthalene, patchouli alcohol, norpathoulenol, isobornyl cyclohexanol, 2,2,7,7-tetramethyltricyclo [6.2.1.0$^{1,6}$]undecane-5-one, octahydro-7,7,8,8-tetramethyl-2,3b-methano-3bh-cyclopenta(1,3)cyclopropa(1, 2)benzene-4-methyl acetate, nootkatone, 9-ethylidene-3-oxatricyclo[6.2.1.0$^{2,6}$]undecane-4-one, cedryl methyl ether, α-pinene, β-pinene, 5,6,7,7a-tetrahydro-4,4,7a-trimethyl-2(4h)-benzofuranone (dihydroactinidolide), 1,3-dimethyl-8-(1-methylethyl)-tricyclo[4.4.0.0.0$^{2,7}$] dec-3-ene (α-copaene), camphene, 4 acetyl-6-tertiarybutyl-1,1-dimethyl indane, 5-acetyl-1,1,2,6-tetramethyl-3-isopropyl-dihydroinden, β-nephthyl isobutyl ether, decahydro-β-naphthyl acetate, 6-methoxydicyclopentadiene carboxaldehyde, 4-methyl tricyclo [6.2.1.0]undecan-5-one, 4,4a,5,8,8a-hexahydro-3',7'-dimethyl spiro(1,4-methanonaphthalene-2(1h), 2'-oxirane), dodecahydro-3a,6,6,9a-tetramethyl-naphto [2,1-b]furan, and 6-ethylidene octahydro-5,8-methano-2h-1-benzopyran-2-one;
d) a fragrance compound containing a single alicyclic ring which contains at least 5 atoms, but no more than 8 atoms, of any of carbon, oxygen, nitrogen and sulfur in which at least one of the carbon atoms of the ring has two substituents, or a carbon atom alpha to the ring is a tertiary carbon atom, or the ring has substituents on at least three of the atoms which make up the ring, and selected from the group consisting of para-tertiary-butyl-cyclohexanol, ortho-tertiary-butyl-cyclohexanol, para-tertiary-butyl-cyclohexanone, γ-ionone, β-damascenone, 4 acetoxy-4-methyl-2-propyl-tetrahydro-2h-pyran, ortho tertiary amyl cyclohexanyl acetate, 2,4-dimethylcyclohexanemethanol, ethyl acetoacetate propylene glycol acetal, isocyclogeraniol, 5-methyl-3-butyltetrahydropyran-4-yl acetate, fenchol, (−)-2-ethyl-4-(2,2,3-trimethyl-3-cyclopenten-1-yl)-2-buten-1-ol, ethylacetoacetate ethyleneglycol ketal, nopol, nopyl acetate, 2,6,6-trimethyl-1-cyclohexen-1-acetoaldehyde, 2,4,6-trimethyl-3-cyclohexene-1-carboxaldehyde, 2,4, 6-trimethyl-3-cyclohexene-1-methanol, 3-methyl-5-propyl-2-cyclohexen-1-one, dynascone (firmenich), α-iso-methyl-ionone, 3,3-dimethyl-5-(2',2',3'-trimethyl-3'-cyclopenten-1'-yl)-4-penten-2-ol, 2,2-dimethyl-6-methylene cyclohexane carboxylic acid methyl ester, 5-pentyl-2,2,5-trimethylcyclopentanone, 2,2,6-trimethyl-α-propyl-cyclohexanepropanol, 2-tert-butyl cyclohexyl oxy-2-butanol, myrac aldehyde, 2-methyl-4-(2,6,6-trimethyl-1-cyclohexen-1-yl)-2-butenal, 2,2,5-trimethyl-5-pentylcyclopentanone, β-2,2,3-tetramethyl-3-cyclopentene-1-butanol, 2-methyl-4-(2,2,3-trimethyl-3-cyclopenten-1-yl)-2-buten-1-ol, 3-methyl-5-(2,2,3-trimethyl cyclopent-3-en-1-yl-pentan-2-ol, 4-tert-pentylcyclohexanone, 4-(1-ethoxyvinyl)-3,3,5,5-tetramethyl cyclohexanone, ethyl 2-tert-butyl cyclohexyl carbonate, methyl 2-hexyl-3-oxocyclopentanecarboxylate, 3-oxo-2-(2-cis-pentenyl)cyclopentane acetic acid methyl ester, and 2-pentyl-3-methyl-2-cyclopenten-1-one;
e) a fragrance compound containing at least one macrocyclic ring, which is a ring having more greater than eight atoms of any of carbon, nitrogen oxygen or sulfur in the ring, and selected from the group consisting of 3 methylcyclopentadecanone, 3-methylcyclopentadecenone, 3-methylcyclopentadecanol, cyclopentadecanone, (Z)-4-cyclopentadecen-1-one, trimethyl-oxabicyclotridecadiene, 15-pentadecenolide, 12-methyl-14-tetradec-9-enolide, oxacycloheptadec-7(or 10)-en-2-one, [3 (or 4)-cyclooctan-1-yl]methyl carbonate, methyl 2,6,10-trimethylcyclododeca-2,5,9-trien-1-yl ketone, cyclodecyl methyl ether, and ethoxyymethoxycyclidodecane;
f) a fragrance compound containing at least one substituted aromatic ring containing at least 5 atoms of any of carbon, oxygen, nitrogen or sulfur, but in which at least one substituents has a tertiary carbon in a position alpha or beta to the ring, and selected from the group consisting of 2-methyl-3-(4-tert-butylphenyl)propanal, 2,5,5-trimethyl-2-phenyl-1,3-dioxane, 4-tert-butylbenzennpropionaldehyde, dimethybenzylcarbinyl acetate, and 5-phenyl-5-methyl-3-hexanone; and g) a fragrance compound containing a substituted aromatic ring comprising at least 5 atoms with at least 3 substituents groups on the ring all of which must contain at least 2 atoms from among carbon, oxygen, nitrogen or sulfur, and selected from the group consisting of 1,3,5-trimethoxybenzene, acetyl eugenol, acetyl vanillin, musk thibetone, musk ambrette, 3,4-dimethoxybenzoic acid, 3,4-methylenedioxybenzyl acetate and veratraldehyde, wherein 40-100% by weight of the at least 5 different fragrance compounds comprise at least 3 bulky molecules having a molecular weight of less than 325 atomic mass units and a C log P value between C log P 1.00 and C log P 4.00, wherein the fragrance composition comprises less than 1% by weight of a fragrance aldehyde, and wherein the other benefit agents are not constrained by the molecular weight restrictions.

2. The fragrance composition according to claim 1, wherein the molecular weights of the individual fragrance ingredients lie within the range 100 to 300 atomic mass units and 80% to 100% by weight of bulky molecules have C log P values greater than 1.0.

3. The fragrance composition according to claim 1, wherein the molecular weights of the individual fragrance ingredients lie within the range 100 to 275 atomic mass units and 80% to 100% by weight of bulky molecules have C log P values greater than 1.0.

4. A fragrance composition to be incorporated into the core of a core shell capsule comprising 60-100% by weight of bulky molecules according to claim 1.

5. A fragrance composition to be incorporated into the core of a core shell capsule comprising 80-100% by weight of bulky molecules according to claim 1.

6. A fragrance composition to be incorporated into the core of a core shell capsule, comprising:

I) 60-100% by weight of at least 5 different fragrance compounds, each of the at least 5 different fragrance compounds possessing any of the following structural features a) to f), and II) 0-40% by weight of other benefit agents which possess any of the following structural features a) to f), pro-fragrances, and solvents:

a) a fragrance compound containing more than one ring, each containing 5 or 6 carbon atoms, no atoms being shared by any of the rings, and selected from the group consisting of methyl n-{4-(4-hydroxy-4-methylpentyl)-3-cyclohexen-1-methylene}-anthranilate, endo 4-(5-methyl1-5-norbornen-2-yl)-pyridine, 2,5,5-trimethyl-2-phenyl1,3-dioxane, isocamphyl cyclohexanol, 2-(2,4-dimethyl-3-cyclohexyl)-5-methyl-5-(1-methylpropyl)-1,3-dioxane, vanillin propylene glycol acetal, indol-hydroxycitronellal schiff s base, dimethyl-2-(5',5',8',8'-tetramethyl-5',6',7',8'-tetrahydro-naphthalen-2'-yl)1,3-dioxolane, 2 cyclohexylidene-2-phenylacetonitrile, benzyl cinnamate, benzyl eugenol, cinnamyl anthranilate, cinnamyl cinnamate, cinnamyl phenyl acetate, 4-methyl-2-phenyltetrahydro-2h-pyran, and dibenzyl ketone;

b) a fragrance compound having at least two rings, each having between 3 and 6 atoms in which any rings share one common atom, and selected from the group consisting of 2-methyl-1,5-dioxaspiro[5.5]undecane, 2,2,3',7',7'-pentamethylspiro(1,3-dioxan-5,2'-norcarane), decahydro-spiro[furan-2(3h), 5'-(4,7-methano-5h-indene)], 3,3-dimethyl-1,5-dioxaspiro[5.5]undecane, 4-methyl-1-oxaspiro[5.5]undecene, and 8-methyl-1-oxaspiro[4.5]decan-2-one;

c) a fragrance compound having at least two rings, each ring containing 5 or 6 carbon atoms in which two rings share at least two adjacent common atoms, and selected from the group consisting of coumarin, methyl naphthyl ketone, isobutylquinoline, 6,7-dihydro-1,1,2,3,3-pentamethyl-4(5h)-indanone, tricyclo decenyl acetate and its homologues tricyclo decenyl propionate and tricyclo decenyl isobutyrate, cedryl methyl ether, 4-(1,3-benzodioxol-5-yl) butan-2-one, 3a-ethyl dodecahydro-6,6,9a-trimethyl naphtho[2,1-b]-furan, 2,5,5-trimethyl-octahydronaphthalen-2-ol, α-cedrene, 8-cedren-13-ol, cedryl methyl ether, α-methyl-3,4-methylenedioxy hydrocinnamic aldehyde, ethyl tricyclo[5,2,1,0]decan-2-carboxylate, 1,4-cineole (470-67-7), 1,8-cineole, borneol, bornyl acetate, isoborneol, isobornyl acetate, isobornyl formate, isobornyl methyl ether, isobornyl propionate, 2-ethyl-5(or 6)-methoxy bicyclo[2.2.1]heptane and 1-ethyl-3-methoxy tricyclo[2.2.1.0$^{2,6}$]heptane, 2-ethylidene-6-isopropoxy bicyclo[2.2.1]heptane, 5' (or 6')-(methylnorborn-5'-en-2'-yl)-2-menthyl-1-en-3-ol, 2-[(1,7,7-trimethybicyclo[2,2,1]hept-2-yl)oxy]-ethanol, 7 acetyl-1,2,3,4,5,6,7,8-octahydro-1,1,6,7-tetramethyl-naphthalene, patchouli alcohol, norpathoulenol, isobornyl cyclohexanol, 2,2,7,7-tetramethyltricyclo[6.2.1.0$^{1,6}$]undecane-5-one, octahydro-7,7,8,8-tetramethyl-2,3b-methano-3bh-cyclopenta(1,3)cyclopropa(1,2)benzene-4-methyl acetate, nootkatone, 9-ethylidene-3-oxatricyclo[6.2.1.0$^{2,7}$]undecane-4-one, cedryl methyl ether, α-pinene, β-pinene, 5,6,7,7a-tetrahydro-4,4,7a-trimethyl-2(4h)-benzofuranone (dihydroactinidolide), 1,3-dimethyl-8-(1-methylethyl)-tricyclo[4.4.0.0.0$^{2,7}$] dec-3-ene (α-copaene), camphene, 4 acetyl-6-tertiary-butyl-1,1-dimethyl indane, 5-acetyl-1,1,2,6-tetramethyl-3-isopropyl-dihydroinden, β-nephthyl isobutyl ether, decahydro-β-naphthyl acetate, 6-methoxydicyclopentadiene carboxaldehyde, 4-methyl tricyclo[6.2.1.0]undecan-5-one, 4,4a,5,8,8a-hexahydro-3',7'-dimethyl spiro(1,4-methanonaphthalene-2(1h), 2'-oxirane), dodecahydro-3a,6,6,9a-tetramethyl-naphto[2,1-b]furan, and 6-ethylidene octahydro-5,8-methano-2h-1-benzopyran-2-one;

d) a fragrance compound containing a single alicyclic ring which contains at least 5 atoms, but no more than 8 atoms, of any of carbon, oxygen, nitrogen and sulfur in which at least one of the carbon atoms of the ring has two substituents, or a carbon atom alpha to the ring is tertiary carbon atom, or the ring has substituents on at least three of the atoms which make up the ring, and selected from the group consisting of para-tertiary-butyl-cyclohexanol, ortho-tertiary-butyl-cyclohexanol, para-tertiary-butyl-cyclohexanone, γ-ionone, β-damascenone, 4 acetoxy-4-methyl-2-propyl-tetrahydro-2h-pyran, ortho tertiary amyl cyclohexanyl acetate, 2,4-dimethylcyclohexanemethanol, ethyl acetoacetate propylene glycol acetal, isocyclogeraniol, 5-methyl-3-butyltetrahydropyran-4-yl acetate, fenchol, (−)-2-ethyl-4-(2,2,3-trimethyl-3-cyclopenten-1-yl)-2-buten-1-ol, ethylacetoacetate ethyleneglycol ketal, nopol, nopyl acetate, 2,6,6-trimethyl-1-cyclohexen-1-acetoaldehyde, 2,4,6-trimethyl-3-cyclohexene-1-carboxaldehyde, 2,4,6-trimethyl-3-cyclohexene-1-methanol, 3-methyl-5-propyl-2-cyclohexen-1-one, dynascone (firmenich), α-iso-methyl-ionone, 3,3-dimethyl-5-(2',2',3'-trimethyl-3'-cyclopenten-1'-yl)-4-penten-2-ol, 2,2-dimethyl-6-methylene cyclohexane carboxylic acid methyl ester, 5-pentyl-2,2,5-trimethylcyclopentanone, 2,2,6-trimethyl-α-propyl-cyclohexanepropanol, 2-tert-butyl cyclohexyl oxy-2-butanol, myrac aldehyde, 2-methyl-4-(2,6,6-trimethyl-1-cyclohexen-1-yl)-2-butenal, 2,2,5-trimethyl-5-pentylcyclopentanone, β-2,2,3-tetramethyl-3-cyclopentene-1-butanol, 2-methyl-4-(2,2,3-trimethyl-3-cyclopenten-1-yl)-2-buten-1-ol, 3-methyl-5-(2,2,3-trimethyl cyclopent-3-en-1-yl-pentan-2-ol, 4-tert-pentylcyclohexanone, 4-(1-ethoxyvinyl)-3,3,5,5-tetramethyl cyclohexanone, ethyl 2-tert-butyl cyclohexyl carbonate, methyl 2-hexyl-3-oxocyclopentanecarboxylate, 3-oxo-2-(2-cis-pentenyl)cyclopentane acetic acid methyl ester, and 2-pentyl-3-methyl-2-cyclopenten-1-one;

e) a fragrance compound containing at least one macrocyclic ring, which is a ring having more greater than eight atoms in the ring, and selected from the group consisting of 3 methylcyclopentadecanone, 3-methylcyclopentadecenone, 3-methylcyclopentadecanol, cyclopentadecanone, (Z)-4-cyclopentadecen-1-one, trimethyl-oxabicyclotridecadiene, 15-pentadecenolide, 12-methyl-14-tetradec-9-enolide, oxacycloheptadec-7(or 10)-en-2-one, [3(or 4)-cycloocten-1-yl]methyl carbonate, methyl 2,6,10-trimethylcyclododeca-2,5,9-trien-1-yl ketone, cyclodecyl methyl ether, and ethoxyymethoxycyclidodecane; and f) a fragrance compound containing at least one substituted benzene ring but in which at least one substituents group processes a tertiary carbon in a position alpha or beta to the ring, and selected from the group consisting of 2-methyl-3-(4-tert-butylphenyl)propanal, 2,5,5-trimethyl-2-phenyl-1,3-dioxane, 4-tert-butylbenzennpropionaldehyde, dimethybenzylcarbinyl acetate, and 5-phenyl-5-methyl-3-hexanone, wherein 40-100% by weight of the at least 5 different fragrance compounds comprise at least 3 bulky molecules having a molecular weight of less than 275 atomic mass units and a C log P value between C log P 1.00 and C log P 4.00, wherein the fragrance composition comprises less than 1% by weight of a fragrance aldehyde, and wherein the other benefit agents are not constrained by the molecular weight restrictions.

7. The fragrance composition according to claim 1 or 6, wherein 60-100% by weight of the fragrance ingredients have C log P values between C log P 1.00 and C log P 4.00.

8. The fragrance composition according to claim 1 or 6, wherein 80-100% by weight of the fragrance ingredients have C log P values between C log P 1.00 and C log P 4.00.

9. The fragrance composition according to claim 1 or 6, wherein more than 25% of the originally encapsulated amount by weight of the individual fragrance components survive storage for 4 weeks at 40° C., when dosed at 0.5% of encapsulated fragrance oil when dispersed in a 10% (wt/wt) aqueous solution of sodium dodecyl sulfate buffered at pH of 8.5.

10. The fragrance composition according to claim 1 or 6, wherein more than 50% of the originally encapsulated amount by weight of the individual fragrance components survive storage for 4 weeks at 40° C., when dosed at 0.5% of encapsulated fragrance oil when dispersed in a 10% (wt/wt) aqueous solution of sodium dodecyl sulfate buffered at pH of 8.5.

11. The fragrance composition according to claim 1 or 6, containing 0-40% weight of one or more benefit agents in which the benefit agents are selected among the group consisting of molodor counteracting agents, essential oils, aromatherapeutic materials, chemoesthetic agents, vitamins, insect repellents, pro-fragrances, UV absorbers, antioxidants and agents to improve the capsule properties such as:
  a) by stabilizing the emulsion during capsule manufacture,
  b) by reducing leakage from the capsule,
  c) by improving capsule hardness.

12. The fragrance composition according to claim 1 or 6, wherein the fragrance contains less than 10% by weight of amines.

13. An encapsulated fragrance comprising a core shell having a thickness of 0.025-1.0 μm and a fragrance composition according to claim 1 or 6.

14. The encapsulated fragrance according to claim 13, wherein the capsule shell is an aminoplast capsule constituted of 50-100% by weight of formaldehyde-melamine or formaldehyde-melamine-urea or formaldehyde-urea condensation polymer.

15. The encapsulated fragrance according to claim 13, wherein the average size of the capsule is between 1-1000 micrometers.

16. A household, laundry or personal care composition which is in the form of a liquid, gel, paste, soft solid, or liquid applied to a fibrous substrate such as a wipe, containing one or more of surfactants and/or solvents containing the core shell capsule according to claim 1.

17. The household, laundry or personal care composition according to claim 16, which is in the form of a liquid having a viscosity greater than 100 mPa·s at 5 s$^{-1}$.

18. The household, laundry or personal care composition according to claim 16, which is in the form of a liquid having a viscosity greater than 1000 mPa·s at 5 s$^{-1}$.

19. The household, laundry or personal care composition according to claim 16, wherein the composition is a liquid laundry detergent, a liquid fabric softener, a hair shampoo, a hair conditioner, a liquid soap, a shower gel, or a liquid impregnated on household or personal care wipes.

20. A household, laundry or personal care composition which is in the form of a liquid, gel, paste, soft solid, or liquid applied to a fiber substrate such as a wipe containing one or more of surfactants and/or solvents containing the core shell capsule according to claim 6.

21. The household, laundry or personal care composition according to claim 20, which is in the form of a liquid having a viscosity greater than 100 mPa·s at 5 s$^{-1}$.

22. The household, laundry or personal care composition according to claim 20, which is in the form of a liquid having a viscosity greater than 1000 mPa·s at 5 s$^{-1}$.

23. The household, laundry or personal care composition according to claim 20, wherein the composition is a liquid laundry detergent, a liquid fabric softener, a hair shampoo, a hair conditioner, a liquid soap, a shower gel, or a liquid impregnated on household or personal care wipes.

* * * * *